United States Patent
Jung et al.

(10) Patent No.: US 10,042,980 B2
(45) Date of Patent: Aug. 7, 2018

(54) PROVIDING ASSISTANCE RELATED TO HEALTH

(75) Inventors: Edward K. Y. Jung, Bellevue, WA (US); Royce A. Levien, Lexington, MA (US); Robert W. Lord, Seattle, WA (US); Mark A. Malamud, Seattle, WA (US); John D. Rinaldo, Jr., Bellevue, WA (US); Lowell L. Wood, Jr., Livermore, CA (US)

(73) Assignee: Gearbox LLC, Bellevue, WA (US)

( * ) Notice: Subject to any disclaimer, the term of this patent is extended or adjusted under 35 U.S.C. 154(b) by 1315 days.

(21) Appl. No.: 11/283,548

(22) Filed: Nov. 17, 2005

(65) Prior Publication Data
US 2007/0112587 A1    May 17, 2007

(51) Int. Cl.

| A61B 5/00 | (2006.01) |
| A61N 1/39 | (2006.01) |
| G06F 19/00 | (2018.01) |
| G06Q 10/08 | (2012.01) |
| G06Q 10/10 | (2012.01) |
| G06Q 30/06 | (2012.01) |
| G06Q 50/22 | (2018.01) |

(52) U.S. Cl.
CPC .......... G06F 19/324 (2013.01); G06F 19/325 (2013.01); G06F 19/326 (2013.01); G06Q 10/087 (2013.01); G06Q 10/10 (2013.01); G06Q 30/0601 (2013.01); G06Q 50/22 (2013.01)

(58) Field of Classification Search
CPC .... G06F 19/322; G06F 19/3456; G06Q 50/22
USPC ....................................................... 705/2–3
See application file for complete search history.

(56) References Cited

U.S. PATENT DOCUMENTS

| 4,293,845 A | 10/1981 | Villa-Real |
| 4,446,138 A | 5/1984 | Pack |
| 4,567,185 A | 1/1986 | Sackner |
| 4,838,275 A | 6/1989 | Lee |
| 4,847,764 A | 7/1989 | Halvorson |
| 4,857,716 A | 8/1989 | Gombrich et al. |
| 5,054,493 A | 10/1991 | Cohn et al. |
| 5,176,285 A | 1/1993 | Shaw |
| 5,279,294 A | 1/1994 | Anderson et al. |
| 5,300,302 A | 4/1994 | Tachon et al. |
| 5,307,263 A | 4/1994 | Brown |
| 5,324,077 A | 6/1994 | Kessler et al. |
| 5,495,961 A | 3/1996 | Maestre |
| 5,537,313 A | 7/1996 | Pirelli |
| 5,542,420 A | 8/1996 | Goldman et al. |

(Continued)

FOREIGN PATENT DOCUMENTS

| WO | WO 97/14393 | 4/1997 |
| WO | WO 99/45354 | 9/1999 |

(Continued)

OTHER PUBLICATIONS

Parlante, Linked List Basics, Apr. 12, 2001, http://cslibrary.stanford.edu/103/LinkedListBasics.pdf, pp. 1-26.*

(Continued)

*Primary Examiner* — Joy Chng

(57) ABSTRACT

In one aspect, a method related to health-related data management. In addition to the foregoing, other method and system and program product aspects are described in the claims, drawings, and text forming a part of the present application.

38 Claims, 16 Drawing Sheets

(56) References Cited

U.S. PATENT DOCUMENTS

| | | | |
|---|---|---|---|
| 5,672,154 A | 9/1997 | Sillén et al. | |
| 5,692,502 A | 12/1997 | Alpert | |
| 5,700,998 A | 12/1997 | Palti | |
| 5,710,578 A | 1/1998 | Beauregard et al. | |
| 5,737,539 A | 4/1998 | Edelson et al. | |
| 5,770,226 A | 6/1998 | Hughes, Jr. et al. | |
| 5,807,579 A | 9/1998 | Vilkov et al. | |
| 5,873,369 A | 2/1999 | Laniado et al. | |
| 5,882,931 A | 3/1999 | Petersen | |
| 5,907,291 A | 5/1999 | Chen et al. | |
| 5,940,801 A | 8/1999 | Brown | |
| 5,954,640 A | 9/1999 | Szabo | |
| 5,955,269 A | 9/1999 | Ghai et al. | |
| 5,968,932 A | 10/1999 | Winokur et al. | |
| 5,985,214 A | 11/1999 | Stylli et al. | |
| 5,995,938 A | 11/1999 | Whaley | |
| 6,021,202 A * | 2/2000 | Anderson | G06F 17/24 705/18 |
| 6,024,699 A | 2/2000 | Surwit et al. | |
| 6,035,230 A | 3/2000 | Kang et al. | |
| 6,108,635 A * | 8/2000 | Herren | G06Q 40/08 705/2 |
| 6,117,073 A | 9/2000 | Jones et al. | |
| 6,128,534 A | 10/2000 | Park et al. | |
| 6,139,494 A | 10/2000 | Cairnes | |
| 6,161,095 A | 12/2000 | Brown | |
| 6,188,988 B1 | 2/2001 | Barry et al. | |
| 6,209,095 B1 | 3/2001 | Anderson et al. | |
| 6,227,371 B1 | 5/2001 | Song | |
| 6,287,595 B1 | 9/2001 | Loewy et al. | |
| 6,383,136 B1 | 5/2002 | Jordan | |
| 6,397,190 B1 | 5/2002 | Goetz | |
| 6,421,650 B1 | 7/2002 | Goetz et al. | |
| 6,450,956 B1 * | 9/2002 | Rappaport | G16H 15/00 600/300 |
| 6,468,805 B1 | 10/2002 | Smith | |
| 6,497,342 B2 | 12/2002 | Zhang et al. | |
| 6,510,430 B1 | 1/2003 | Oberwager et al. | |
| 6,529,446 B1 | 3/2003 | de la Huerga | |
| 6,541,478 B1 | 4/2003 | O'Malley et al. | |
| 6,586,478 B2 | 7/2003 | Ackman et al. | |
| 6,589,169 B1 | 7/2003 | Surwit et al. | |
| 6,609,200 B2 | 8/2003 | Anderson et al. | |
| 6,616,606 B1 | 9/2003 | Petersen et al. | |
| 6,656,122 B2 | 12/2003 | Davidson et al. | |
| 6,671,818 B1 | 12/2003 | Mikurak | |
| 6,699,193 B2 | 3/2004 | Crutchfield et al. | |
| 6,735,593 B1 | 5/2004 | Williams | |
| 6,764,831 B2 | 7/2004 | Cameron, Sr. et al. | |
| 6,770,029 B2 | 8/2004 | Iliff | |
| 6,790,198 B1 | 9/2004 | White et al. | |
| 6,833,274 B2 | 12/2004 | Lawrence et al. | |
| 6,898,761 B2 | 5/2005 | Anderson et al. | |
| 6,951,545 B2 | 10/2005 | Smith et al. | |
| 6,955,873 B1 | 10/2005 | Blum | |
| 7,005,447 B2 | 2/2006 | Ahotupa et al. | |
| 7,016,752 B1 | 3/2006 | Ruben et al. | |
| 7,029,441 B2 | 4/2006 | Dodds | |
| 7,135,616 B2 | 11/2006 | Heard et al. | |
| 7,136,820 B1 | 11/2006 | Petrus | |
| 7,169,432 B2 | 1/2007 | Tanaka et al. | |
| 7,172,897 B2 | 2/2007 | Blackburn et al. | |
| 7,193,128 B2 | 3/2007 | Copenhaver et al. | |
| 7,197,492 B2 | 3/2007 | Sullivan | |
| 7,216,343 B2 | 5/2007 | Das et al. | |
| 7,280,975 B1 | 10/2007 | Donner | |
| 7,295,889 B2 | 11/2007 | Lahteenmaki | |
| 7,312,243 B1 | 12/2007 | Pravda | |
| 7,351,739 B2 | 4/2008 | Ho et al. | |
| 7,376,585 B2 | 5/2008 | Haller | |
| 7,379,167 B2 | 5/2008 | Mawhirt et al. | |
| 7,418,399 B2 | 8/2008 | Schaeffer et al. | |
| 7,454,880 B1 | 11/2008 | Austin et al. | |
| 7,461,006 B2 | 12/2008 | Gogolak | |
| 7,483,839 B2 | 1/2009 | Mayaud | |
| 7,490,085 B2 | 2/2009 | Walker et al. | |
| 7,502,666 B2 | 3/2009 | Siegel et al. | |
| 7,635,594 B2 | 12/2009 | Holmes et al. | |
| 7,844,609 B2 | 11/2010 | Kenedy et al. | |
| 7,957,984 B1 | 6/2011 | Vallone | |
| 8,135,595 B2 | 3/2012 | Dalton | |
| 2001/0037340 A1 | 11/2001 | Hawkins et al. | |
| 2001/0039503 A1 | 11/2001 | Chan et al. | |
| 2002/0016719 A1 | 2/2002 | Nemeth et al. | |
| 2002/0023172 A1 | 2/2002 | Gendron et al. | |
| 2002/0026111 A1 | 2/2002 | Ackerman | |
| 2002/0027164 A1 | 3/2002 | Mault et al. | |
| 2002/0032580 A1 | 3/2002 | Hopkins | |
| 2002/0032583 A1 | 3/2002 | Joao | |
| 2002/0033753 A1 | 3/2002 | Imbo | |
| 2002/0038392 A1 | 3/2002 | De La Huerga | |
| 2002/0047867 A1 | 4/2002 | Mault et al. | |
| 2002/0049738 A1 | 4/2002 | Epstein | |
| 2002/0065682 A1 | 5/2002 | Goldenberg | |
| 2002/0091546 A1 | 7/2002 | Christakis et al. | |
| 2002/0099686 A1 | 7/2002 | Schwartz et al. | |
| 2002/0106429 A1 | 8/2002 | Mudar et al. | |
| 2002/0111932 A1 | 8/2002 | Roberge et al. | |
| 2002/0116225 A1 | 8/2002 | Morse et al. | |
| 2002/0128259 A1 | 9/2002 | Ghazzi et al. | |
| 2002/0143434 A1 | 10/2002 | Greeven et al. | |
| 2002/0147317 A1 | 10/2002 | Bentsen et al. | |
| 2002/0147917 A1 | 10/2002 | Brickell | |
| 2002/0156651 A1 | 10/2002 | Florio et al. | |
| 2002/0156683 A1 | 10/2002 | Stoutenburg et al. | |
| 2002/0192310 A1 | 12/2002 | Bland et al. | |
| 2002/0194221 A1 | 12/2002 | Strong et al. | |
| 2002/0196141 A1 | 12/2002 | Boone et al. | |
| 2003/0004403 A1 | 1/2003 | Drinan et al. | |
| 2003/0005445 A1 | 1/2003 | Schein et al. | |
| 2003/0010791 A1 | 1/2003 | Gentiluomo et al. | |
| 2003/0028399 A1 | 2/2003 | Davis et al. | |
| 2003/0032069 A1 | 2/2003 | Muraca | |
| 2003/0032868 A1 | 2/2003 | Graskov et al. | |
| 2003/0036683 A1 | 2/2003 | Kehr et al. | |
| 2003/0046114 A1 | 3/2003 | Davies et al. | |
| 2003/0069757 A1 | 4/2003 | Greenberg | |
| 2003/0072770 A1 | 4/2003 | McAnalley et al. | |
| 2003/0073931 A1 | 4/2003 | Boecker et al. | |
| 2003/0082544 A1 | 5/2003 | Fors et al. | |
| 2003/0086338 A1 | 5/2003 | Sastry et al. | |
| 2003/0099158 A1 | 5/2003 | De la Huerga | |
| 2003/0114475 A1 | 6/2003 | Fox et al. | |
| 2003/0135388 A1 | 7/2003 | Martucci et al. | |
| 2003/0137067 A1 | 7/2003 | Cooper et al. | |
| 2003/0139655 A1 | 7/2003 | Dodds | |
| 2003/0158756 A1 | 8/2003 | Abramson | |
| 2003/0163353 A1 | 8/2003 | Luce et al. | |
| 2003/0186001 A1 | 10/2003 | Khan | |
| 2003/0194350 A1 | 10/2003 | Stamatelos et al. | |
| 2003/0204412 A1 | 10/2003 | Brier | |
| 2003/0208381 A1 | 11/2003 | Walter et al. | |
| 2003/0219812 A1 | 11/2003 | Quay et al. | |
| 2003/0229455 A1 | 12/2003 | Bevilacqua et al. | |
| 2003/0233124 A1 | 12/2003 | Hara et al. | |
| 2003/0233250 A1 | 12/2003 | Joffe et al. | |
| 2003/0233257 A1 | 12/2003 | Matian et al. | |
| 2003/0236683 A1 | 12/2003 | Henderson et al. | |
| 2004/0001874 A1 | 1/2004 | Davidson et al. | |
| 2004/0006491 A1 | 1/2004 | Brown et al. | |
| 2004/0026447 A1 | 2/2004 | Badin et al. | |
| 2004/0039599 A1 | 2/2004 | Fralic | |
| 2004/0064342 A1 * | 4/2004 | Browne | A61N 1/39 705/2 |
| 2004/0078220 A1 | 4/2004 | Jackson | |
| 2004/0078236 A1 | 4/2004 | Stoodley et al. | |
| 2004/0084895 A1 | 5/2004 | Blum | |
| 2004/0088187 A1 | 5/2004 | Chudy et al. | |
| 2004/0088374 A1 | 5/2004 | Webb et al. | |
| 2004/0093331 A1 | 5/2004 | Garner et al. | |
| 2004/0111298 A1 | 6/2004 | Schoenberg | |
| 2004/0116780 A1 | 6/2004 | Brown | |
| 2004/0121767 A1 | 6/2004 | Simpson et al. | |
| 2004/0122661 A1 | 6/2004 | Hawkinson et al. | |

(56) References Cited

U.S. PATENT DOCUMENTS

| | | |
|---|---|---|
| 2004/0122707 A1 | 6/2004 | Sabol et al. |
| 2004/0122790 A1 | 6/2004 | Walker et al. |
| 2004/0138926 A1 | 7/2004 | Ishikawa et al. |
| 2004/0143403 A1 | 7/2004 | Brandon et al. |
| 2004/0146592 A1 | 7/2004 | Garrity et al. |
| 2004/0176984 A1 | 9/2004 | White et al. |
| 2004/0215486 A1 | 10/2004 | Braverman |
| 2004/0220498 A1 | 11/2004 | Li et al. |
| 2004/0221855 A1 | 11/2004 | Ashton |
| 2004/0225203 A1 | 11/2004 | Jemison et al. |
| 2004/0243437 A1 | 12/2004 | Grace et al. |
| 2004/0243441 A1 | 12/2004 | Bocionek et al. |
| 2004/0254868 A1 | 12/2004 | Kirkland et al. |
| 2005/0014134 A1 | 1/2005 | West et al. |
| 2005/0021413 A1 | 1/2005 | Berry et al. |
| 2005/0027570 A1 | 2/2005 | Maier et al. |
| 2005/0033121 A1 | 2/2005 | Modrovich |
| 2005/0033773 A1 | 2/2005 | Roberge et al. |
| 2005/0038558 A1 | 2/2005 | Keene |
| 2005/0038674 A1 | 2/2005 | Braig et al. |
| 2005/0061336 A1 | 3/2005 | Goetz et al. |
| 2005/0070607 A1 | 3/2005 | Andrus et al. |
| 2005/0075794 A1 | 4/2005 | Hoffman et al. |
| 2005/0080651 A1 | 4/2005 | Morrison et al. |
| 2005/0090718 A1 | 4/2005 | Dodds |
| 2005/0101841 A9 | 5/2005 | Kaylor et al. |
| 2005/0102159 A1 | 5/2005 | Mondshine |
| 2005/0113649 A1 | 5/2005 | Bergantino |
| 2005/0118202 A1 | 6/2005 | Yamashita et al. |
| 2005/0118241 A1 | 6/2005 | Landschaft |
| 2005/0147667 A1 | 7/2005 | Rines |
| 2005/0149354 A1 | 7/2005 | Cyr et al. |
| 2005/0158401 A1 | 7/2005 | Morris |
| 2005/0180962 A1 | 8/2005 | Raz et al. |
| 2005/0182653 A1* | 8/2005 | Urban .................. G06F 19/3456 705/2 |
| 2005/0191716 A1 | 9/2005 | Surwit et al. |
| 2005/0192487 A1 | 9/2005 | Cosentino et al. |
| 2005/0211768 A1 | 9/2005 | Stillman |
| 2005/0216313 A1 | 9/2005 | Claud et al. |
| 2005/0216390 A1 | 9/2005 | Snider et al. |
| 2005/0228245 A1 | 10/2005 | Quy |
| 2005/0240085 A1 | 10/2005 | Knoell et al. |
| 2005/0256745 A1 | 11/2005 | Dalton |
| 2005/0260610 A1 | 11/2005 | Kurtz et al. |
| 2005/0260679 A1 | 11/2005 | Kellerman et al. |
| 2005/0261255 A1 | 11/2005 | Serhan et al. |
| 2005/0267356 A1 | 12/2005 | Ramasubramanian et al. |
| 2005/0271596 A1 | 12/2005 | Friedman et al. |
| 2006/0010009 A1 | 1/2006 | Fangman |
| 2006/0010090 A1 | 1/2006 | Brockway et al. |
| 2006/0047538 A1 | 3/2006 | Condurso et al. |
| 2006/0064250 A1 | 3/2006 | Goldstein |
| 2006/0073099 A1 | 4/2006 | Frincke et al. |
| 2006/0089542 A1 | 4/2006 | Sands |
| 2006/0090765 A1 | 5/2006 | Surina |
| 2006/0111944 A1 | 5/2006 | Sirmans, Jr. et al. |
| 2006/0129324 A1 | 6/2006 | Rabinoff et al. |
| 2006/0136259 A1 | 6/2006 | Weiner et al. |
| 2006/0161443 A1 | 7/2006 | Rollins |
| 2006/0177637 A1 | 8/2006 | Kimura |
| 2006/0240150 A1 | 10/2006 | Delaney et al. |
| 2006/0248468 A1 | 11/2006 | Constantine et al. |
| 2006/0254580 A1 | 11/2006 | Chalmers et al. |
| 2006/0260679 A1 | 11/2006 | Aratani et al. |
| 2006/0264780 A1 | 11/2006 | Holmes et al. |
| 2006/0281770 A1 | 12/2006 | Kase et al. |
| 2006/0287891 A1 | 12/2006 | Grasso et al. |
| 2007/0018810 A1 | 1/2007 | Smythe et al. |
| 2007/0035403 A1 | 2/2007 | Krishna et al. |
| 2007/0065506 A1 | 3/2007 | Kelly et al. |
| 2007/0067186 A1 | 3/2007 | Brenner et al. |
| 2007/0068959 A1 | 3/2007 | D'Silva |
| 2007/0087048 A1 | 4/2007 | Abrams et al. |
| 2007/0093448 A1 | 4/2007 | Westermann et al. |
| 2007/0118054 A1 | 5/2007 | Pinhas et al. |
| 2007/0136092 A1 | 6/2007 | Jung et al. |
| 2007/0161076 A1 | 7/2007 | Halden |
| 2007/0192134 A1 | 8/2007 | Littenberg et al. |
| 2008/0097784 A1 | 4/2008 | Miller et al. |
| 2008/0100279 A1 | 5/2008 | Mohapatra et al. |
| 2008/0139907 A1 | 6/2008 | Roa et al. |
| 2008/0208027 A1 | 8/2008 | Heaton |
| 2008/0299013 A1 | 12/2008 | Trieu et al. |
| 2009/0198176 A1 | 8/2009 | Chavez et al. |
| 2010/0081144 A1 | 4/2010 | Holmes et al. |

FOREIGN PATENT DOCUMENTS

| | | |
|---|---|---|
| WO | WO 00/60362 | 10/2000 |
| WO | WO 01/79529 A1 | 10/2001 |
| WO | WO 2004/082359 A2 | 9/2004 |
| WO | WO 2005/018632 A1 | 3/2005 |
| WO | WO 2005/062849 A2 | 7/2005 |
| WO | WO 2007/061838 A2 | 5/2007 |

OTHER PUBLICATIONS

Parlante, Linked List Basics, Apr. 12, 2001, http://cslibrary.stanford.edu/103/LinkedListBasics.pdf, pp. 1-26 (Year: 2001).*
U.S. Appl. No. 11/355,517, Jung et al.
U.S. Appl. No. 11/339,316, Jung et al.
U.S. Appl. No. 11/314,949, Jung et al.
U.S. Appl. No. 11/314,945, Jung et al.
U.S. Appl. No. 11/314,764, Jung et al.
U.S. Appl. No. 11/291,532, Jung et al.
U.S. Appl. No. 11/291,482, Jung et al.
U.S. Appl. No. 11/285,753, Jung et al.
U.S. Appl. No. 11/285,500, Jung et al.
PCT International Search Report; International App. No. PCT/US 06/44664; dated Apr. 14, 2008; pp. 1-3.
PCT International Search Report; International App. No. PCT/US07/25379; dated May 13, 2008; pp. 1-2.
PCT International Search Report; International App. No. PCT/US07/25417; dated May 14, 2008; pp. 1-3.
PCT International Search Report; International App. No. PCT/US07/25417; dated May 19, 2008; pp. 1-2.
PCT International Search Report; International App. No. PCT/US2007/025450; dated May 23, 2008; pp. 1-2.
PCT International Search Report; International App. No. PCT/US06/47835; dated Jul. 14, 2008; pp. 1-2.
PCT International Search Report; International App. No. PCT/ US 06/44278; 2 pages; dated Aug. 17, 2007.
PCT International Search Report; International App. No. PCT/ US 06/44269; 2 pages; dated Sep. 18, 2007.
Cover, Robin, ed.; "Technology Reports: General SGML/XML Applications" [see e.g. "SGML Initiative in Health Care (HL7 Health Level-7 and SGML/XML)"]; Cover Pages: Hosted by Oasis; Bearing a date of Nov. 11, 2002, printed on Nov. 16, 2005; pp. 1-95; located at: http://xml.coverpages.org/gen-apps.html.
Goedert, Joseph, ed.; "XML Comes of Age for Data Exchange"; Health Data Management; Bearing dates of Nov. 16, 2005 and 2005, printed on Nov. 16, 2005; pp. 1-4; SourceMedia, Inc; located at: http://www.healthdatamanagement.com/html/current/CurrentIssueStory.cfm?PostID=16205.
Guo, Jinqiu; Araki, Kenji; Tanaka, Koji; Sato, Junzo; Suzuki, Muneou; Takada, Akira; Suzuki, Toshiaki; Nakashima, Yusei; Yoshihara, Hiroyuki; "The Latest MML (Medical Markup Language) Version 2.3—XML-Based Standard for Medical Data Exchange/Storage"; Journal of Medical Systems; Bearing dates of Aug. 2003 and 2003; pp. 357-366; vol. 27, No. 4; Plenum Publishing Corporation; located at: http://lob.kuhp.kyoto-u.ac.jp/paper/200308mml23JMS/mml23JMS.pdf.
Kahn Jr., Charles E.; De La Cruz, Norberto B.; "Extensible Markup Language (XML) in Health Care: Integration of Structured Reporting and Decision Support"; Office of Clinical Informatics; pp. 1-5; located at: http://www.amia.org/pubs/symposia/D004673.PDF.

(56) References Cited

OTHER PUBLICATIONS

McDonald, Carol; Srinivas, Raghavan N.; "How Java Technology and XML Are Improving Healthcare in Brazil"; Java.sun.com; Bearing dates of Feb. 2004 and 1994-2005, printed on Nov. 16, 2005; pp. 1-9; Sun Microsystems, Inc.; located at: http://java.sun.com/developer/technicalArticles/xml/brazil/index.html.

Smith, Stevie; "New Chip Identifies Bird Flu in Humans"; The Tech Herald.com, WOTR Limited; 2008; located at: www.thetechherald.com/article/php200813/520/new-chip-identifies-bird-flu-in-humans; Bearing a date of Mar. 25, 2008; printed on Sep. 8, 2008; pp. 1-6.

PCT International Search Report; International App. No. PCT/US2007/025451; dated Sep. 15, 2008; pp. 1-2.

PCT International Search Report; International App. No. PCT/US07/20272; dated Sep. 15, 2008; pp. 1-2.

PCT International Search Report; International App. No. PCT/US07/20305; dated Sep. 11, 2008; pp. 1-2.

PCT International Search Report; International App. No. PCT/US07/20283; dated Sep. 11, 2008; pp. 1-2.

PCT International Search Report; International App. No. PCT/US07/14994; dated Sep. 9, 2008; pp. 1-2.

PCT International Search Report; International App. No. PCT/US2008/007993; dated Sep. 8, 2008; pp. 1-3.

PCT International Search Report; International App. No. PCT/US06/47451; dated Sep. 5, 2008; pp. 1-2.

PCT International Search Report; International App. No. PCT/US06/44658; dated Aug. 29, 2008; pp. 1-2.

PCT International Search Report; International App. No. PCT/US06/44279; dated Aug. 19, 2008; pp. 1-3.

PCT International Search Report; International App. No. PCT/US06/44283; dated Aug. 18, 2008; pp. 1-2.

PCT International Search Report; International App. No. PCT/US07/14266; dated Jul. 21, 2008; pp. 1-2.

Evans, R. Scott, Ph.D. et al., "A Computer-Assisted Management Program for Antibiotics and Other Antiinfective Agents"; The New England Journal of Medicine; bearing a date of Jan. 22, 1998; pp. 232-238; vol. 338, No. 4; The Departments of Clinical Epidemiology (R.S.E., S.L.P., D.C.C., J.F.L., J.P.B.), Critical Care (T.P.C., L.K.W., J.F.O.,), and Medical Informatics (R.S.E.), LDS Hospital, Salt Lake City, UT.

Lagally, E.T. et al.; "Integrated Portable Genetic Analysis Microsystem for Pathogen/Infectious Disease Detection"; Analytical Chemistry; bearing a date of Jun. 1, 2004; pp. 3162-3170; vol. 76, No. 11; © 2004 American Chemical Society.

Leibovici, Leonard et al.; "A Causal Probabilistic Network for Optimal Treatment of Bacterial Infections"; IEEE Transactions on Knowledge and Data Engineering; bearing a date of Jul./Aug. 2000; pp. 517-528; vol. 12, No. 4; © 2000 IEEE.

Mullett, Charles J. et al.; "Computerized antimicrobial decision support: an offline evaluation of a database-driven empiric antimicrobial guidance program in hospitalized patients with a bloodstream infection"; International Journal of Medical Informatics; 2004; pp. 455-460; vol. 73; Elsevier Ireland Ltd.

Sriskanthan, N. and Subramanian, K. R.; "Braille Display Terminal for Personal Computers"; IEEE Transactions on Consumer Electronics; May 1990; pp. 121-128; vol. 36, No. 2; IEEE.

UK Intellectual Property Office Examination Report Under Section 18(3); App. No. GB1000316.8; dated Jul. 26, 2011; pp. 1-3.

Walt et al.; "Biological Warfare, a Host of Detection Strategies Have Been Developed, But Each Has Significant Limitations"; Analytical Chemistry; bearing a date of Dec. 1, 2000; pp. 738A-747A.

U.S. Appl. No. 13/374,765, Jung et al.

Krishna et al.; "Glutathione and γ-glutamyl transpeptidase are differentially distributed in the olfactory mucosa of rats"; Cell Tissue Res; bearing a date of Jul. 1992; pp. 475-484; vol. 270; Springer-Verlag.

"Component"; IEEE Xplore Digital Library; printed on Oct. 3, 2013; 1 page; IEEE; located at: http://ieeexplore.ieee.org/xpls/dictionary.jsp?stdDiet=match_keyword&def_term=component.

"GARLIC Nature's Amazing Nutritional and Medicinal Wonder Food"; pp. 1-32; Bearing a date of 1995, Created on Jul. 3, 2014, as provided by examiner; Woodland Publishing, Inc.; Pleasant Grove, UT.

Sabate et al; "Handbook of Nutraceuticals and Functional Foods, Chapter 28: The Role of Nuts in Cardiovascular Disease Prevention"; pp. 1-19; Bearing a date of 2001, Created on Jul. 3, 2014, as provided by examiner; CRC Press LLC.

"Microsoft Press Computer Dictionary: The Comprehensive Standard for Business, School, Library, and Home"; bearing a date of Nov. 1, 1993; 1 page; Edition 2; Microsoft Press; ISSN: 9781556155970 (whole book not provided).

Roberts et al.; "Nutraceuticals: The Complete Encyclopedia of Supplements, Herbs, Vitamins and Healing Foods"; American Nutraceutical Association; bearing a date of Jan. 1, 2001; pp. 1-3 (669 pages, not provided); Perigee Trade; IBSN: 0399526323 (whole book not provided).

Edible Science; bearing dates of 2005-2010; pp. 1-2; located at: http://www.ediblescience.com; printed on May 13, 2010.

Fightermins; bearing a date of 2010; 1 page; located at: http://www.fightermins.com/index.jsp; printed on May 13, 2010.

Ideal Health; "Custom Essentials"; "The Priva Test"; bearing a date of 2010; total of 5 pages; located at: http://www.idealhealth.com; printed on May 13, 2010; The Trump Network.

I-Vita; bearing a date of 2009; 1 page; located at: http://www.mynutrapack.com/index.html; printed on May 13, 2010.

LifeScript; bearing dates of 1998-2010; 1 page; located at: http://vitamins.lifescript.com/Begin.asp?BID=14971&PROMO=zluswiec; printed on May 13, 2010.

Mindell, Earl, Dr.; Vitaganic "Custom-Made Multivitamins"; bearing dates of 2005-2010; 1 page; located at: http://drmindell.vitaganic.com/; printed on May 13, 2010.

My Vitamin Clinic; bearing a date of 2010; 1 page; located at: http://www.myvitaminclinic.com/index.jsp; printed on May 13, 2010.

MyNutraPack; 1 page; located at: http://www.mynutrapack.com/index.html; printed on May 25, 2010.

MyVitaminRx; bearing a date of 2007; 1 page; located at: http://www.myvitaminsrx.com/CustomNutrition.aspx?ID=MoonlightSpa; printed on May 13, 2010.

Nature Made; pp. 1-2; located at: http://www.naturemade.com/; printed on May 13, 2010.

NutriHerb; bearing dates of 2001-2009; pp. 1-2; Nutri Herb, Inc.; located at: http://www.nutriherb.net/custom_made_to_order_herbal_vitamins_supplements.html; printed on May 13, 2010.

Pharmavite LLC; 1 page; located at: http://www.pharmavite.com/index.asp; printed on May 13, 2010.

"Pharmavite LLC Launches New Direct-To-Consumer Company" Press Release; Pharmavite LLC; bearing a date of Sep. 4, 2009; 1 page; located at: http://www.pharmavite.com/MediaCenter/MC_PR.asp?ID=164; printed on May 13, 2010.

Signature Supplements; bearing a date of 2009; pp. 1-2; located at: http://www.signaturesupplements.com/jsp/main/index.jsp; printed on May 13, 2010; Signature Supplements.

Soyjoy®; bearing a date of 2010; 1 page; located at: http://www.soyjoy.com/index.aspx; printed on May 13, 2010; Pharmavite LLC.

Total Health Nutrients; pp. 1-2; located at: http://www.totalhealthnutrients.com/ph/index.html; printed on May 13, 2010.

VitaminID.com; bearing a date of 2010; 1 page; located at: http://www.vitaminid.com/webapp/wcs/stores/servlet/StoreView?storeId=201&langId=-1; printed on May 25, 2010; Pharmavite Direct LLC.

Vitamins on Demand; bearing a date of 2010; 1 page; located at: http://www.vitaminsondemand.com/?gclid=CNbygPut9aACFRYhDQodyGkivw; printed on May 13, 2010.

VitaXact; bearing a date of 2009; 1 page; located at: http://www.vitaxact.com; printed on May 13, 2010.

(56) References Cited

OTHER PUBLICATIONS

Weil, Andrew, M.D.; "Dr. Weil's Vitamin Advisor & Complete Program Supplements"; bearing a date of 2010; 1 page; located at: https://www.drweilvitaminadvisor.com/drw/ecs/Va2/land_goog_08girl.html?aid=999910&aparam=TSAsGoogleApr10VA_vitamins&refcd=GO000000101882154s_vitamins&tsacr=GO3784957603&gclid=CM3NpLzm9aACFRYhDQodyGkivw; printed on May 13, 2010; Weil Lifestyle Custom Pak.

\* cited by examiner

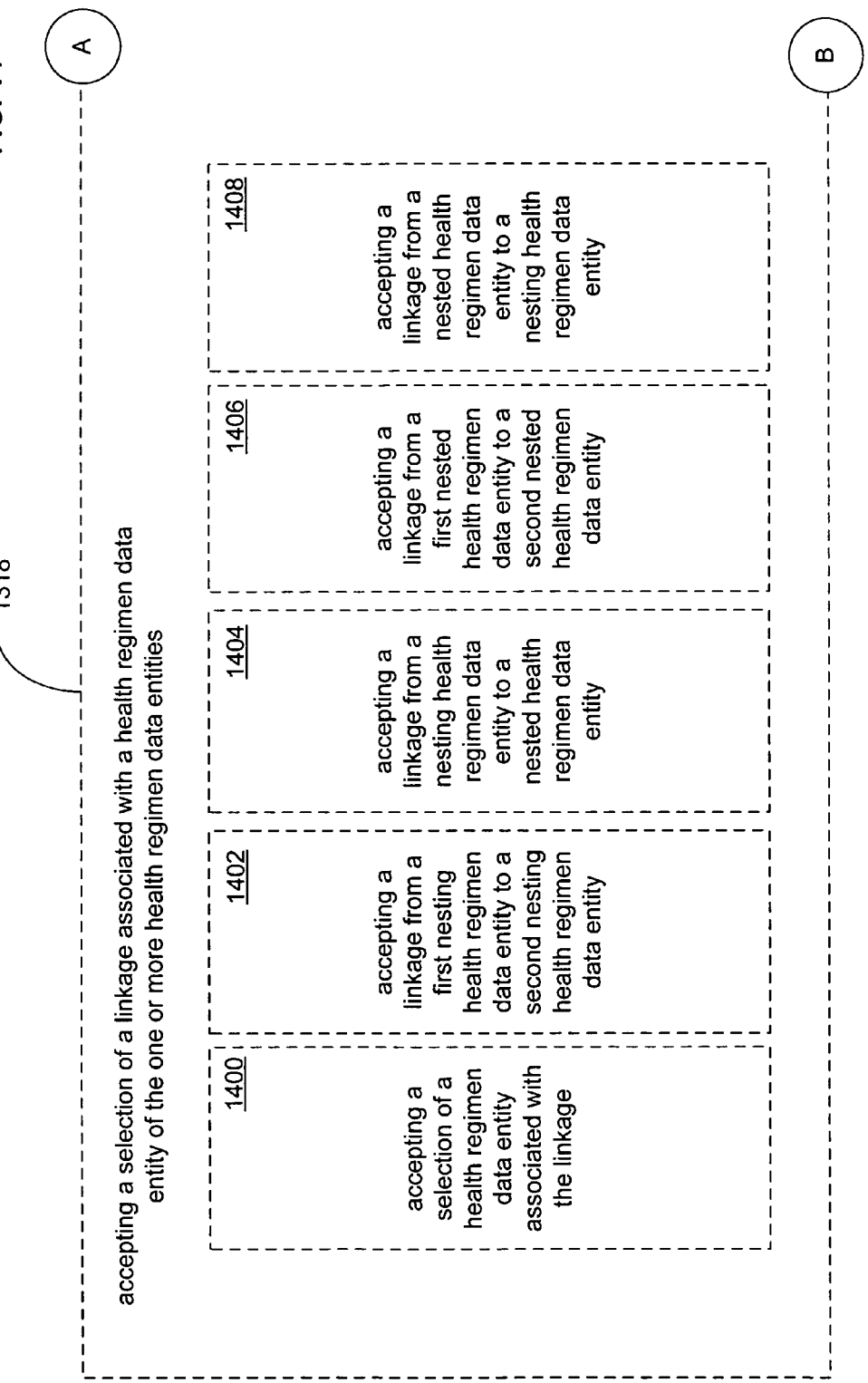

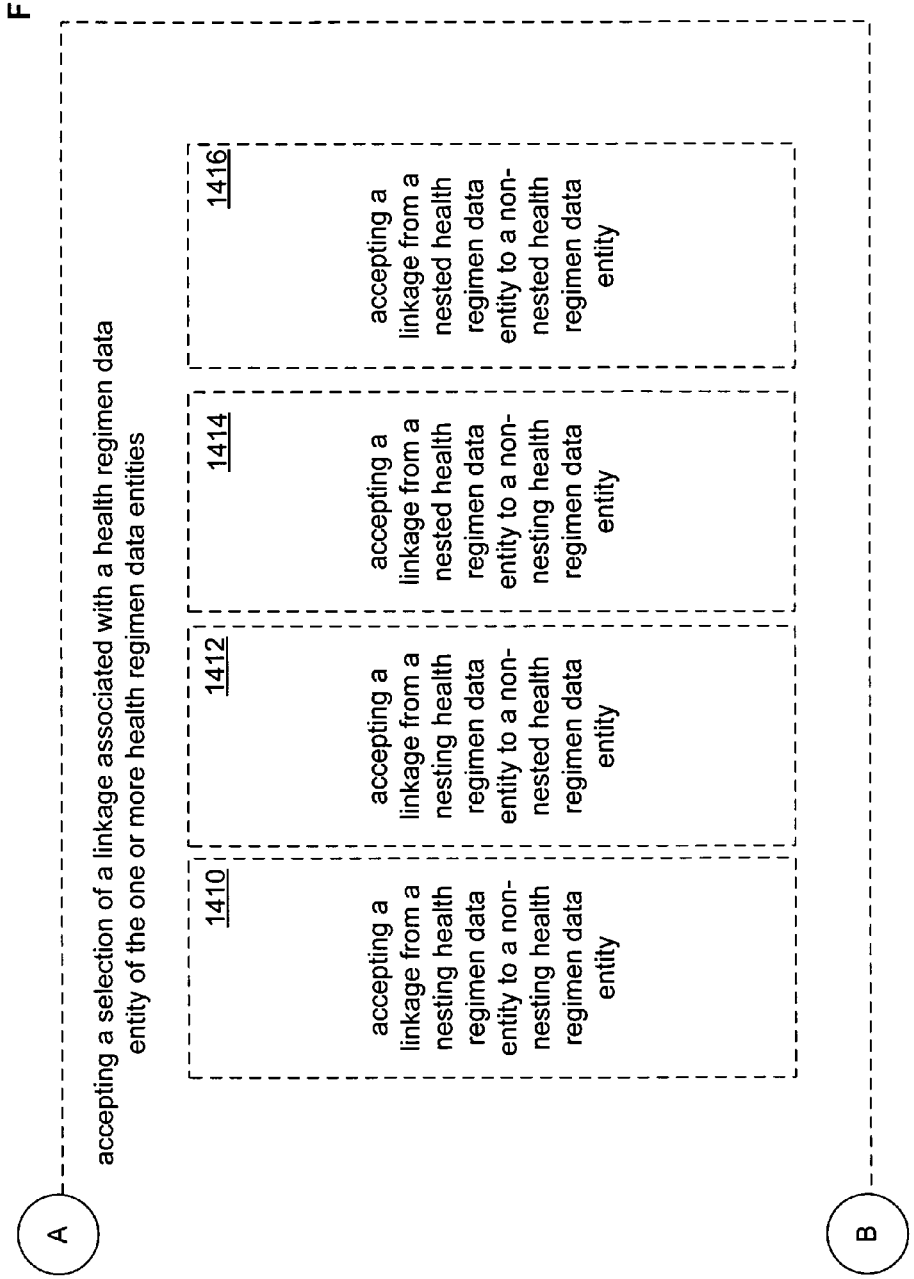

PROVIDING ASSISTANCE RELATED TO HEALTH

TECHNICAL FIELD

The present application relates, in general, to health-related data management.

SUMMARY

In one aspect, a method related to health-related data management includes but is not limited to accepting a change to one or more health regimen data entities. The method may also include, without being limited to, accepting a selection of a linkage associated with a health regimen data entity of the one or more health regimen data entities. In addition to the foregoing, other method aspects are described in the claims, drawings, and text forming a part of the present application.

In one aspect, a system related to health-related data management includes but is not limited to circuitry for accepting a change to one or more health regimen data entities. The system may also include, without being limited to, circuitry for accepting a selection of a linkage associated with a health regimen data entity of the one or more health regimen data entities. In addition to the foregoing, other system aspects are described in the claims, drawings, and text forming a part of the present application.

In one or more various aspects, related systems include but are not limited to circuitry and/or programming and/or electro-mechanical devices and/or optical devices for effecting the herein-referenced method aspects; the circuitry and/or programming and/or electromechanical devices and/or optical devices can be virtually any combination of hardware, software, and/or firmware configured to effect the herein-referenced method aspects depending upon the design choices of the system designer skilled in the art.

In one aspect, a program product includes but is not limited to a signal bearing medium bearing one or more instructions for accepting a change to one or more health regimen data entities. The program product may also include, without being limited to, one or more instructions for accepting a selection of a linkage associated with a health regimen data entity of the one or more health regimen data entities. In addition to the foregoing, other program product aspects are described in the claims, drawings, and text forming a part of the present application.

In addition to the foregoing, various other method, system, and/or program product aspects are set forth and described in the teachings such as the text (e.g., claims and/or detailed description) and/or drawings of the present application.

The foregoing is a summary and thus contains, by necessity, simplifications, generalizations and omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE FIGURES

FIG. 14 shows several alternative implementations of the high-level logic flowchart of FIG. 13.

The use of the same symbols in different drawings typically indicates similar or identical items.

DETAILED DESCRIPTION

Figure 1:
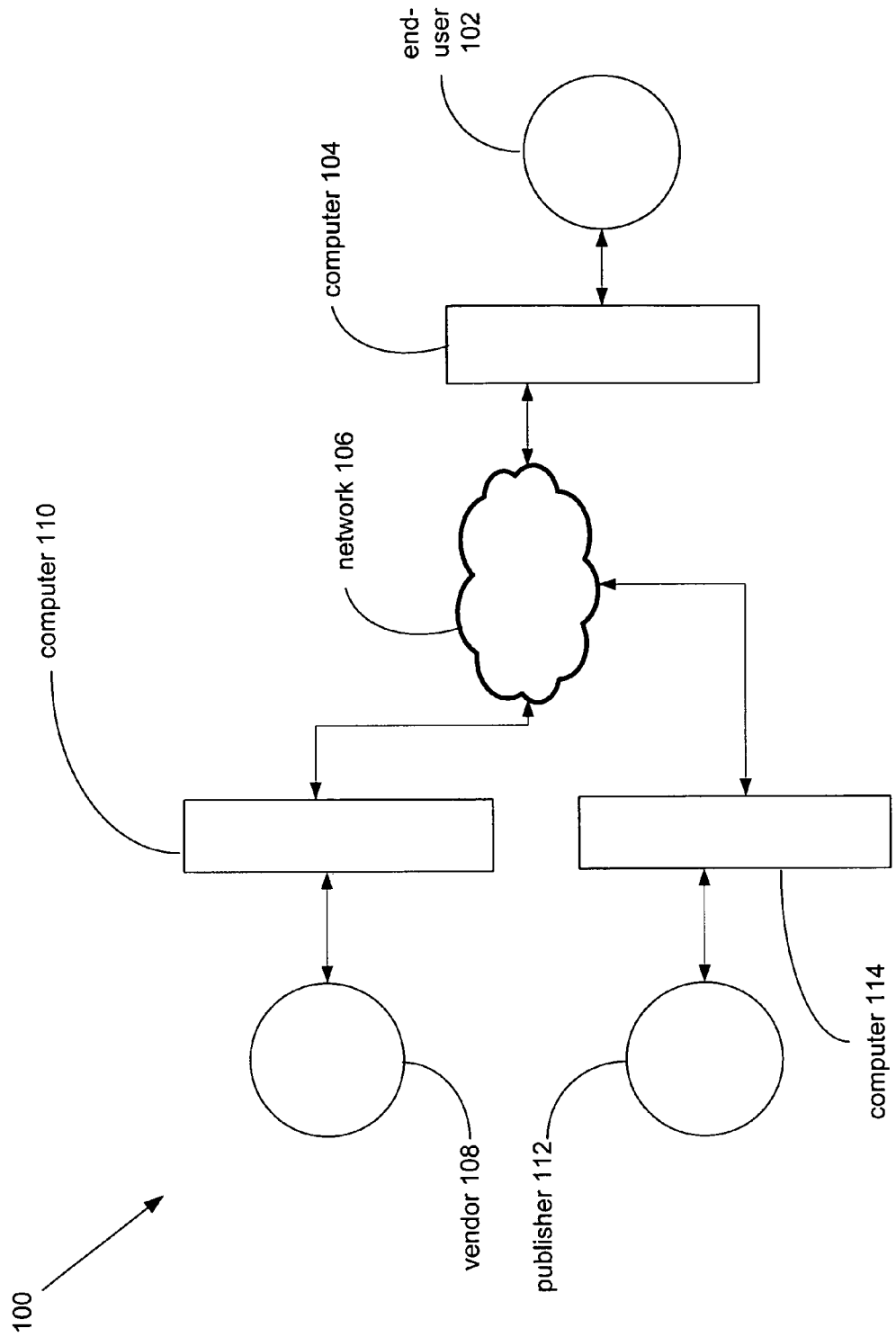
FIG. 1 depicts one implementation of an exemplary environment in which the methods and systems described herein may be represented.

FIG. 1 illustrates an exemplary environment 100 in which embodiments may be used. The end-user 102 is a person who wishes to access information regarding pharmaceutical, nutraceutical, veterinary, dietary, and/or nutritional substances, procedures, processes, and/or practices of interest. The computer 104 is a computer that may be used by the end-user 102 to access such information via another computer or computers represented by the network 106.

Vendor 108 is a person and/or persons and/or entity and/or entities that may supply pharmaceutical, nutraceutical, veterinary, dietary, and/or nutritional substances, procedures, processes, and/or practices of interest. The vendor 108 may use a computer 110 to add information and channels making themselves available to provide pharmaceutical, nutraceutical, veterinary, dietary, and/or nutritional substance, procedure, processes, and/or practices of interest, via another computer or computers represented by the network 106, to, among others, the end-user 102.

Publisher 112 is a person and/or persons and/or entity and/or entities that may supply information about pharmaceutical, nutraceutical, veterinary, dietary, and/or nutritional substances procedures, processes, and/or practices of interest, and/or about authorities having expertise or claimed expertise regarding pharmaceutical, nutraceutical, veterinary, dietary, and/or nutritional substances procedures, processes, and/or practices of interest. The publisher 112 may use a computer 114 to provide such information, via another computer or computers represented by the network 106, to, among others, the end-user 102. The publisher 112 represents a wide variety of information providers, including but not limited to magazine publishers, book publishers, website maintainers, weblog proprietors, experts, research organizations, and users of the pharmaceutical, nutraceutical, veterinary, dietary, and/or nutritional substances procedures, processes, and/or practices of interest.

End-users 102, vendors 108, and publishers 112 are not necessarily mutually exclusive categories. One person, group of persons, entity, or group of entities may be categorized as an end-user 102, vendor 108, and/or publisher 112 simultaneously or at different times. End-users 102, vendors 108, and publishers 112 are exemplary parties and do not represent all users. Exemplary descriptions including the end-user 102 are not limiting and do not preclude use of an embodiment by vendors 108 and/or publishers 112.

Figure 2:
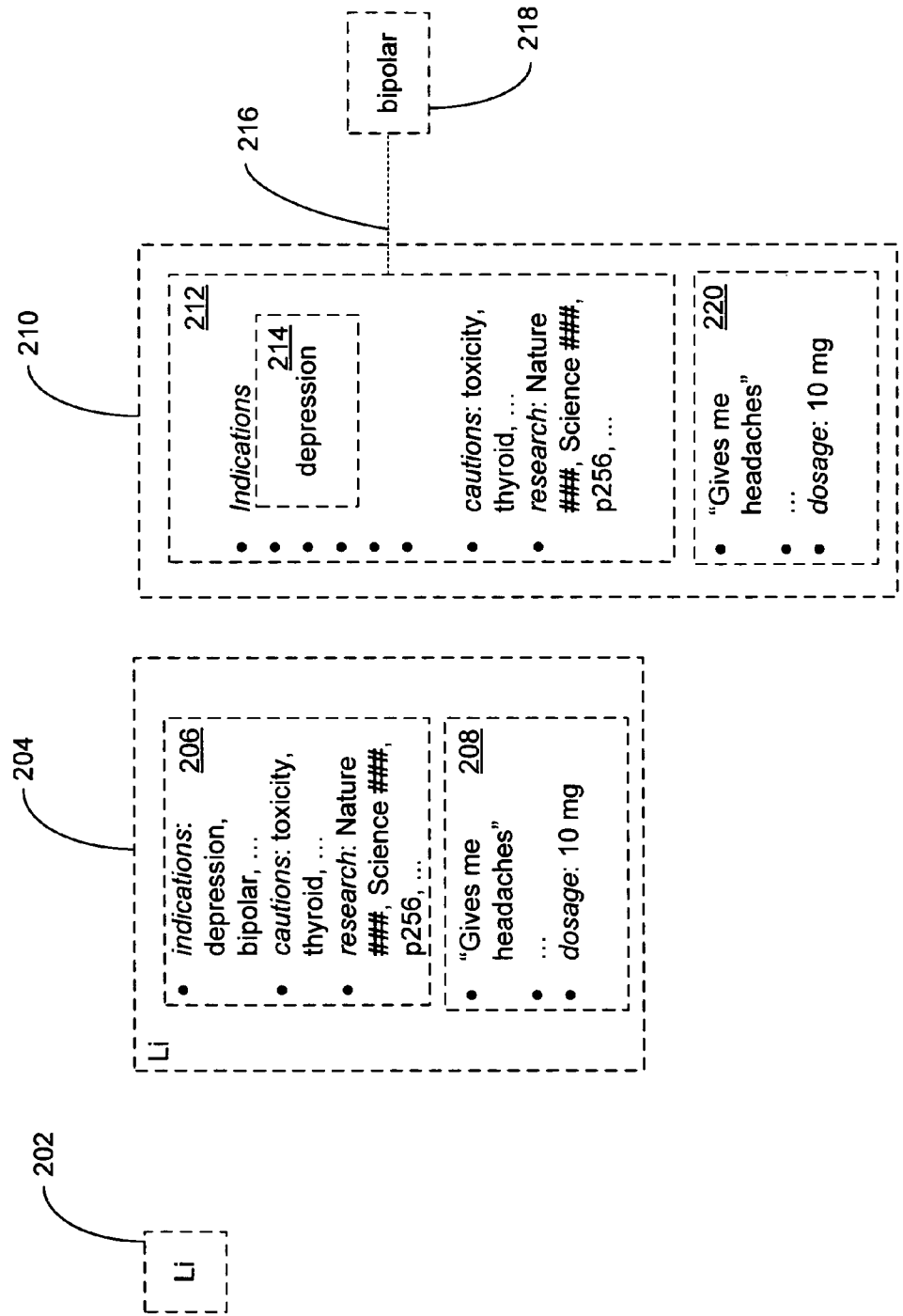
FIG. 2 depicts alternative exemplary embodiments.

FIG. 2 depicts alternative exemplary embodiments of a data entity, including depiction of alternative exemplary embodiments of health regimen data entities associated with some amount of additional information. This additional information may include but is not limited to an item of associative information, i.e., a linkage or a resolvable reference, to one or more other health regimen data entities in the data structure/data structures (e.g., which may be distributed data structures), e.g., a pointer, identifier, and/or a link. In FIG. 2 and the other figures, items of associative data are depicted by lines and/or arrows between health regimen data entities, or are implicit of the relationship between a nesting health regimen data entity and any health regimen data entity nested within or at any depth; such implicit items of associative data are shown by the illustrated nesting. The additional information may also include but is not limited to substantive information, e.g., where the health regimen data entity includes the identity of a substance and the additional information describes a potential use or specifies a dosage. Here health regimen data entity 202 includes an identifier for the element lithium (Li). The health regimen data entity 204 illustrates an alternative exemplary embodiment of the health regimen data entity 202. The end-user 102 may select the health regimen data entity 202 to access additional information that is included in association with the health regimen data entity 202. The additional information may be organized in some defined way, as illustrated in organizational structure 206, or unorganized as in collection 208. The health regimen data entity 210 shows another alternative exemplary embodiment of the health regimen data entity 202. Here the additional information is illustrated as being included in an organizational structure 212. One of the items of additional information associated with the organizational structure 212 is depicted as another health regimen data entity 214 "nested" within health regimen data entity 212. Another of the items of additional information associated with the health regimen data entity 212 is linked by an item of associative information 216 to another health regimen data entity 218. Organizational principles such as those illustrated by the relationship between health regimen data entity 212 and health regimen data entity 214, and by the relationship between health regimen data entity 212, item of associative information 216, and health regimen data entity 218, may be replicated at any level of an organizational structure, or in an unorganized collection such as collection 220. It is to be understood that in substantially all examples referring to "an identifier for lithium" herein, analogous examples utilizing the alternatives such as those from FIG. 2, will be recognized by those of skill in the art. Such examples are not expressly set forth herein for the sake of clarity.

Figure 3:
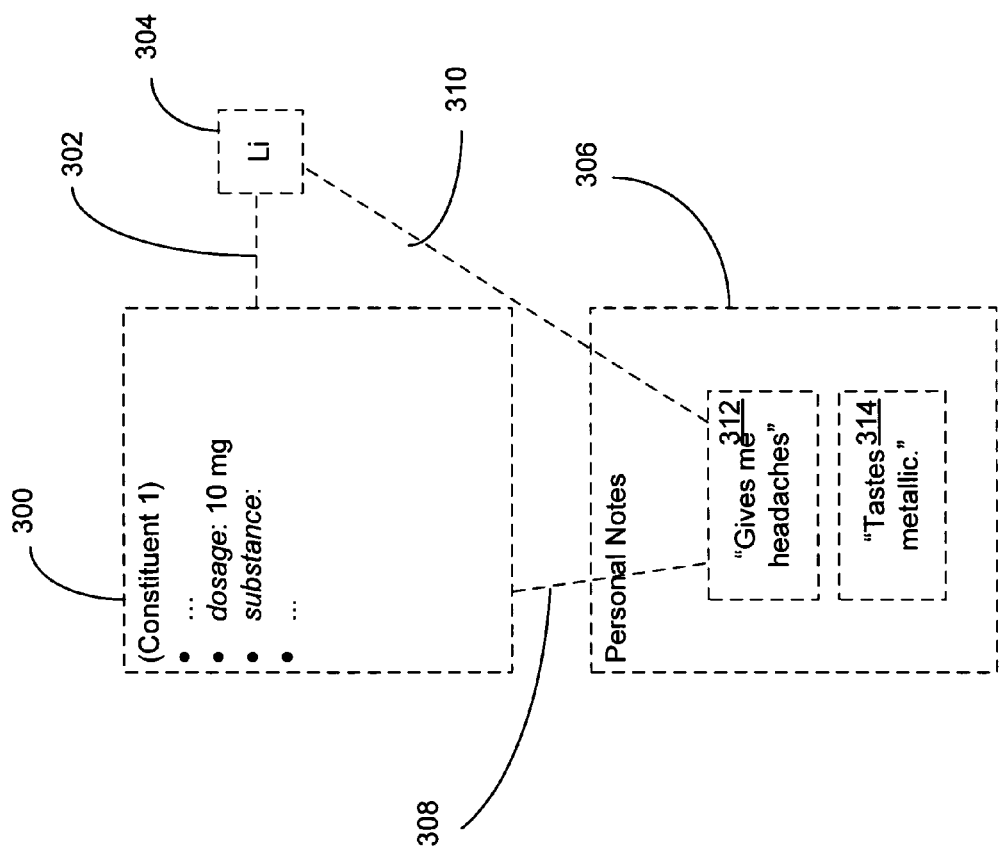
FIG. 3 illustrates alternative exemplary embodiments.

FIG. 3 illustrates an alternative exemplary embodiment of a health regimen data entity. Depicted is nesting health regimen data entity 300, which includes additional information relevant in the context of the nesting health regimen data entity 300, here, "constituent 1." The identity of constituent 1 is not nested within nesting health regimen data entity, but an item of associative data 302 links to a health regimen data entity 304 identifying lithium ("Li"). Also illustrated is a health regimen data entity 306 having additional information detailing personal notes from users of constituent 1. Shown are nested health regimen data entity 312 and 314. The health regimen data entity 312 is linked to the nesting health regimen data entity 300 by an item of associative data 308 and to the health regimen data entity 304 by an item of associative data 310.

Figure 4:
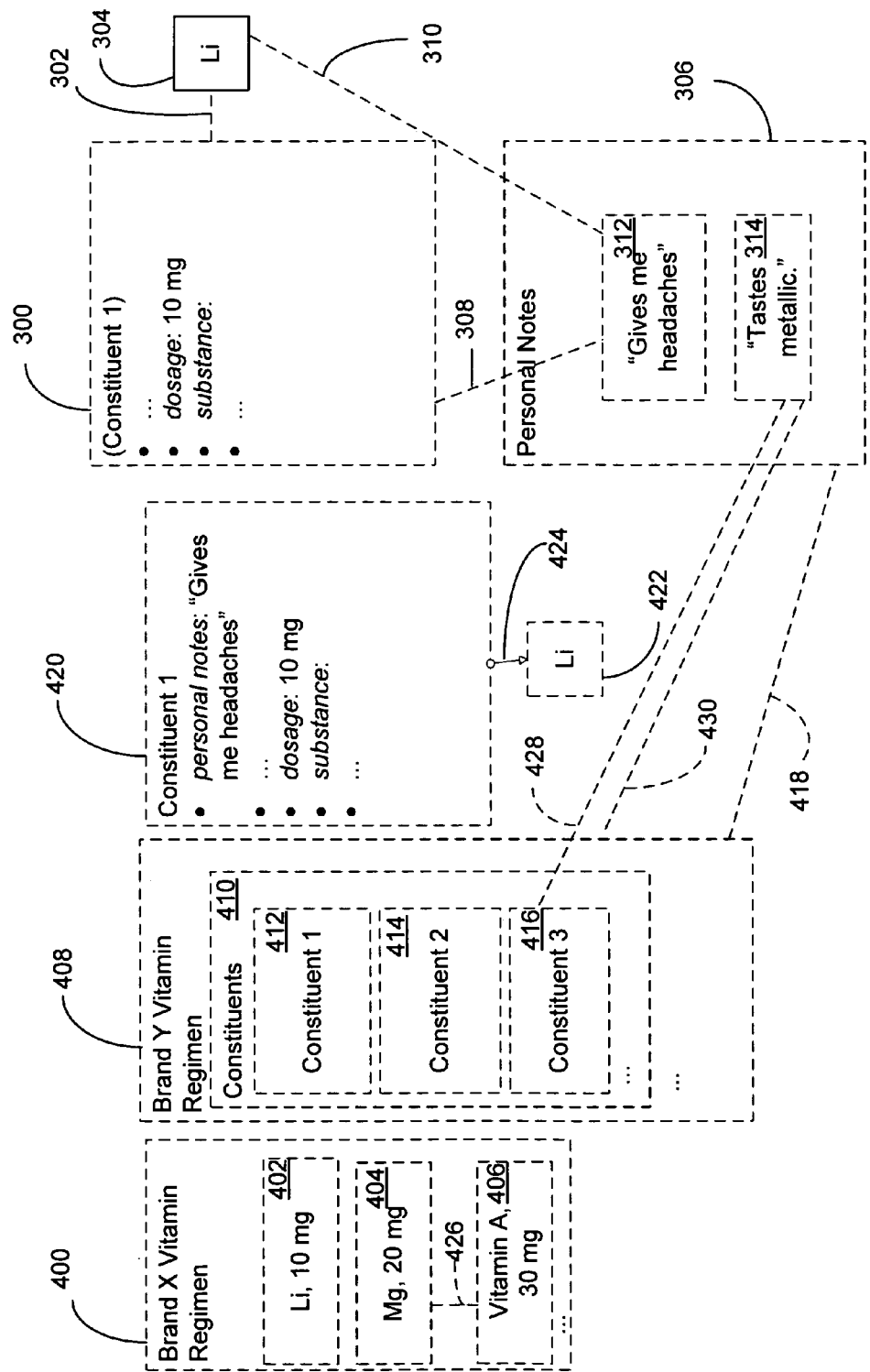
FIG. 4 illustrates alternative exemplary embodiments.

FIG. 4 illustrates a number of alternative exemplary health regimen data entities organized in the data structure according to different organizational schemes. Shown is nesting health regimen data entity 400, including three nested health regimen data entities 402, 404, and 406, for three components of a "Brand X" vitamin regimen. Depicted is nesting health regimen data entity 408, including a nested and nesting health regimen data entity 410. Nested and nesting health regimen data entity 410 includes nested health regimen data entities 412, 414, and 416, components of a "Brand Y" vitamin regimen. Illustrated is nesting health regimen data entity 408 associated with health regimen data entity 306 with an item of associative data 418, linking the personal notes of health regimen data entity 306 with the "Brand Y" vitamin regimen of nesting health regimen data entity 408. Illustrated is health regimen data entity 420, pertaining to "constituent 1," including additional information about personal notes, dosage, and substances. The health regimen data entity 420 is shown linked to health regimen data entity 422, identifying Lithium, by an item of associative data 424. The health regimen data entity 406 is shown linked to another health regimen data entity 404 by an item of associative data 426. The health regimen data entity 314 is shown linked to the health regimen data entity 416 by an item of associative data 428. The health regimen data entity 314 is also shown linked to health regimen data entity 416 by an item of associative data 430.

Figure 5:
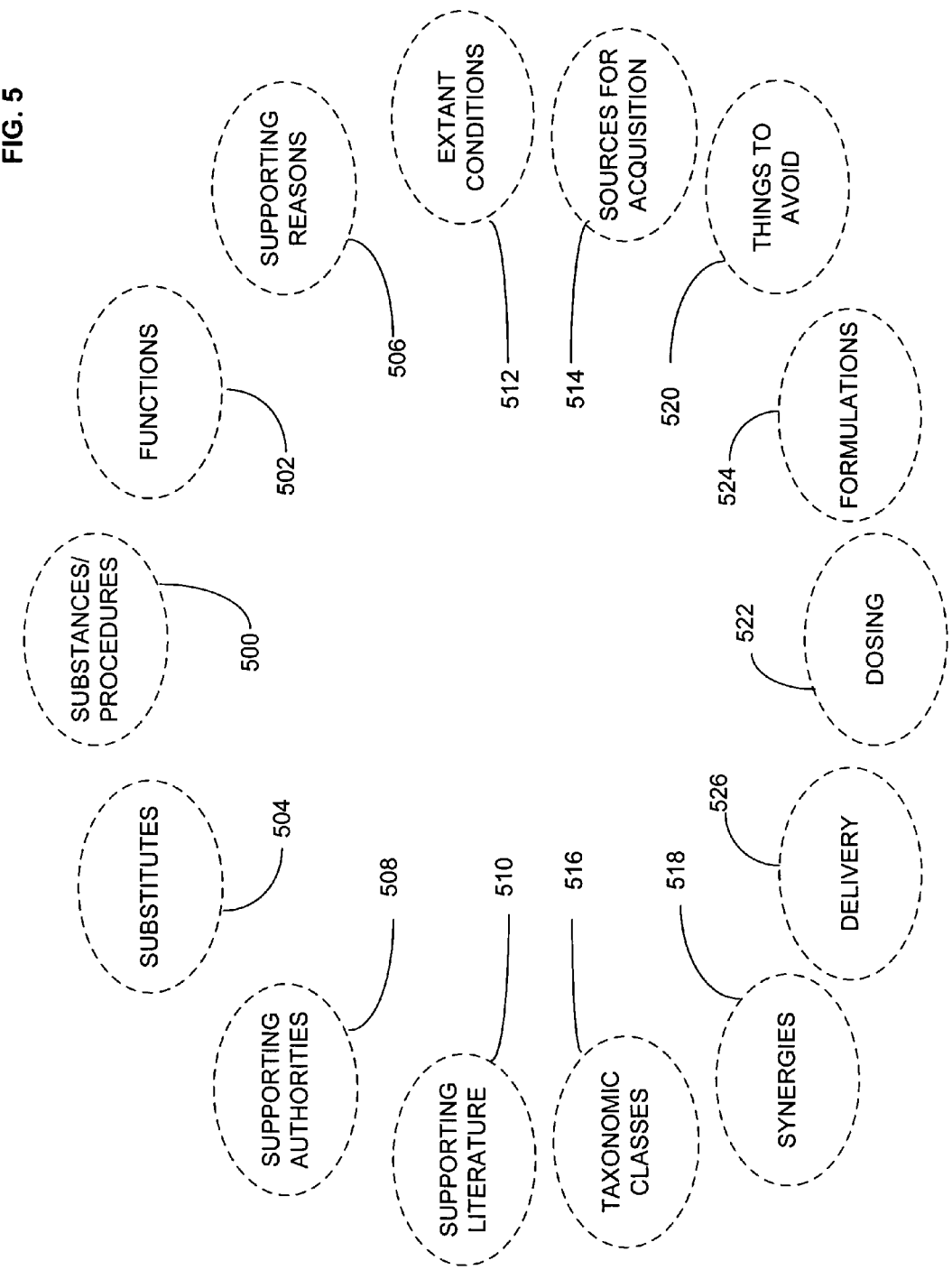
FIG. 5 depicts alternative exemplary aspects of embodiments.

The nesting as illustrated in FIGS. 3, 4, and 5 is accomplished with items of associative information that are associated with either the nesting health regimen data entity or with one or more of the illustrated nested health regimen data entities. The nesting health regimen data entity might represent, e.g., the name of a vitamin supplement, and the nested health regimen data entities might represent, e.g., five constituent supplements comprised by the named vitamin supplement. In another example, the nesting health regimen data entities might represent identifiers of taxonomic classifications to which the constituent belongs, such as chemical classes (such as water soluble or fat soluble vitamins), classes of effect or action (such as beta-blockers, neurotransmitters, or strength enhancers).

A health regimen data entity may be associated with another health regimen data entity in a variety of ways. The first health regimen data entity may be associated with the second health regimen data entity with an item of associative information associated with one or the other or both. The first health regimen data entity may be associated with the second health regimen data entity as well as with additional health regimen data entities simultaneously. The multiply-referenced health regimen data entity may actually be multiple health regimen data entities in the data structure, or it may be a single health regimen data entity with multiple items of associative information used to reference it.

FIG. 5 depicts a number of alternative exemplary topics which may be used in the data structure. The identity of a topic may be represented by a health regimen data entity, and association with a topic accomplished by use of an item of associative information. At least some health regimen data entities may be associated with topics of interest to the end-user 102 to provide a schema with which to begin use of the information in the data structure. Each of the topics is exemplary, but they serve to illustrate a particular application which is not limiting. An end-user 102 may start retrieving data from the data structure by starting with any topic in the data structure. Each item of data stored in association with each topic may have associated using an item of associative information with another item of data associated with the same topic or with another topic, such that an end-user 102 starting with an item of data in a particular topic, e.g., a name of Substance A under the topic Substances/Procedures, may choose to retrieve another item of data associated with Substance A via a an item of associative information to a health regimen data entity associated with another topic, e.g., a function of Substance A, relief of joint pain, associated with the topic Functions. The end-user 102 may continue by selecting an item of data associated with a third topic, e.g., a Substitute B for Substance A for the relief of joint pain, associated with the topic Substitutes. The end-user 102 may continue in this fashion through all of the data items in the topics in the data structure associated via items of associative information to the selections of the end-user 102.

Although shown for clarity in FIG. 5 as discrete topics, generally, topics may be associated with or even be composed of other topics, and a given topic or reference to that topic may be associated with another discrete topic.

The topic 500, "Substances/Procedures," may include common, generic, commercial, and/or trade names and/or descriptions for pharmaceutical, nutraceutical, veterinary, dietary, and/or nutritional substances, procedures, processes, and/or practices of interest to an end-user 102.

The topic 502, "Functions," may include one or more descriptions of functions for which the substances of the topic 500, "Substances/Procedures" may be used by humans in connection with human physical and/or mental conditions, and/or veterinary purposes.

The topic 504, "Substitutes," may include common, generic, commercial, and/or trade names and/or descriptions for pharmaceutical, nutraceutical, veterinary, dietary, and/or nutritional substances, procedures, processes, and/or practices of interest to an end-user 102, which may be substituted to perform functions associated with the topic 502, "Functions."

The topic 506 "Supporting Reasons," may include explanations for the functionality of the substances/procedures and substitutes included in the topics 500, "Substances/Procedures" and 504, "Substitutes."

The topic 508, "Supporting Authorities," may include the identities and credentials of people and/or entities which endorse the use of substances/procedures and substitutes for various functions. The supporting authorities may include medical and/or veterinary professionals and/or experts of various kinds ("gurus"), and/or manufacturers and/or distributors of substances/procedures and substitutes. The topic 508, "Supporting Authorities," may also include testimonials and/or reports and/or anecdotal evidence from other end-users 102, and may include descriptors of factors associated with those end-users 102 to permit manual or automatic correlation of their experience with the potential experience of the end-user 102 consulting the data structure.

The topic 510, "Supporting Literature," may include references to published articles and/or other publicly available information, by citation and/or hyperlink and/or other reference means, e.g., referred journal articles and/or magazine articles and/or website articles, pertaining to the functionality of substances/procedures and substitutes.

The topic 512, "Extant Conditions," may include one or more selections of descriptors that describe internal physical and/or mental and/or environmental and/or spiritual and/or metaphysical factors of interest to the end-user 102 and of possible relevance to the functionality of substances/procedures and substitutes. Internal physical factors may include body temperature, medical condition, genetic information, and/or substances/procedures or substitutes ingested or to be ingested. Mental factors may include a diagnosed mental condition, a subjective mental state, genetic information, and/or substances/procedures or substitutes ingested or to be ingested. Environmental factors may include external temperature, humidity, barometric pressure, ambient light intensity, and, for some, the date, the positions of the planets, geographical factors such as those relevant to feng shui, and/or other factors relevant to disciplines, traditions, and arts considered relevant by the end-user 102 and/or by a contributor of information to the data structure and/or by a third-party authority such as an expert or a source for acquisition. Where feasible, values for external factors may be provided to the data structure in the form of health regimen data entities representing the output of instrumentation, e.g., weather instrumentation or medical instrumentation.

The topic 514, "Sources for Acquisition," may include identities of, contact information for, and/or channels of communication with persons and/or entities from which substances/procedures or substitutes may be purchased or otherwise acquired by the end-user 102. Such sources may pay to be included in the data structure in association with this topic.

The topic 516, "Taxonomic Classes," may include various categories with which substances/procedures and/or substitutes may be associated, e.g. acids, derivatives from X, etc.

The topic 518, "Synergies," may include substances/procedures, substitutes, activities, and/or extant conditions that, acting together with a substance or substitute, enhance the functionality of the substance or substitute; favorably change the amount or timing or the substance or substitute needed for the desired functionality; and/or provide one or more additional desirable functionalities beyond those associated with the substance or substitute taken by itself.

The topic 520, "Things to Avoid," may include substances/procedures, substitutes, activities, and/or extant conditions that, acting together with a substance or substitute, detracts from the functionality of the substance or substitute; unfavorably changes the amount or timing or the substance or substitute needed for the desired functionality; and/or provides one or more additional undesirable functionalities beyond those associated with the substance or substitute taken by itself.

The topic 522, "Dosing," may include information pertaining to the mode, amount, conditions, and/or timing of the delivery of a substance or substitute to achieve the desired functionality, along with synergies and things to avoid, e.g., 200 mg capsules of Substance A, taken twice daily when sunny and thrice daily when cloudy or raining; or once daily under any conditions no matter the weather, and never to be taken when Substance B has been taken within 24 hours. Beyond that simple example, the topic 522, "Dosing," may include a procedure for determining an amount and/or timing for the substance to be taken, rather than a simple fixed value, along with factors that give the end-user 102 options based on probabilities and other factors such as extant conditions, e.g., when the weather is hot and the end-user 102 is feeling irritable, an option to reduce a lithium dose by one pill per day, and if that does not work, by two pills per day, but never by more than two pills per day. These options and alternatives to them may also be accessed by associations with other health regimen data entities, including, e.g., hot days, lithium, and/or irritability.

The topic 524, "Formulations," may include information pertaining to the constituents of a substance, including but not limited to the identities of the constituents, the amounts of the constituents present per unit of the substance, and/or the method(s) for combining the constituents to form the substance. In particular, the amounts of the constituents may be represented by listing the amounts numerically, and/or by a formula or formulas from which each constituent amount may be derived either by the end-user 102 or by computational resources associated with the data structure. In an embodiment, the end-user 102 may follow items of associative information to health regimen data entities and/or additional information that provide information on the sources of formulary information, e.g., an article on an experiment, or on the instruments that provided the formulary information, e.g., an indication of what the underlying methodology of selection is at least partially based upon (e.g., animal studies, human studies, in silico studies, speculation, anecdotal information, historical accounts, traditions, cultural practices, native practices, etc.

The topic 526, "Delivery," may include information on methods of delivery, e.g., orally by capsule, orally by liquid dose, epidermally by patch, injection by syringe, and/or internally by timed release from an implanted reservoir, and on formulations, dose sizes, and dose timings associated with various delivery methods.

Figure 6:
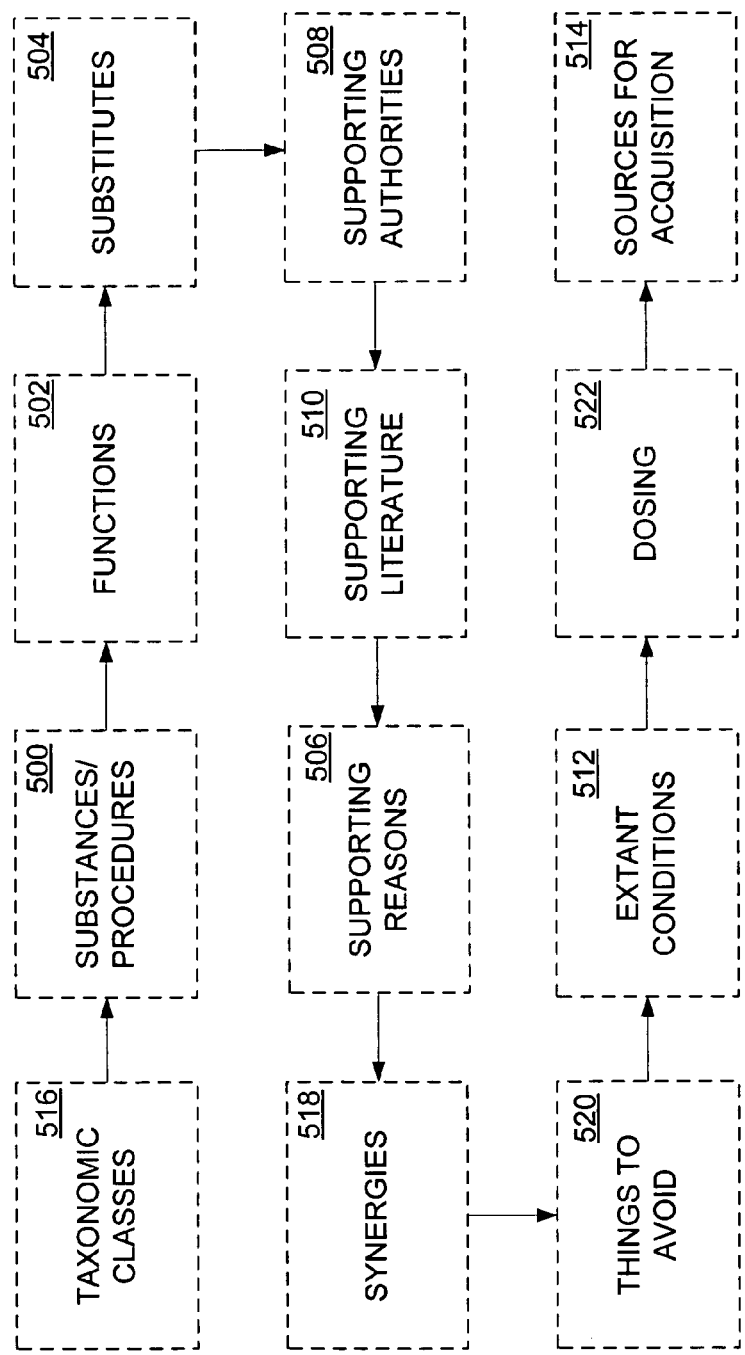
FIG. 6 depicts an exemplary view of aspects of an embodiment.

FIG. 6 depicts an exemplary way to view a pathway on an end-user 102 through data in the data structure. The end-user 102 in this exemplary view starts with taxonomic classes, e.g. vitamins, selects a vitamin, e.g., Vitamin X, and selects an associated function, e.g., increased energy. The end-user 102 finds a substitute for Vitamin X for increasing energy, e.g., Substance Y, refers to supporting authorities, e.g., a particular columnist for a magazine, supporting literature, e.g., an article in JAMA, and supporting reasons, e.g., a web-based explanation for the effects of Substance Y on energy. From there, the end-user 102 calls up information on synergies, e.g., Substance Z as being synergistic with Substance Y, providing increased memory when they are used together, along with things to avoid, e.g., not using Substance W in conjunction with Substance X because such conjunctive use causes impotence. The end-user 102 may consult "Extant Conditions" to learn that Substance X has an increased effect at lower altitudes and/or when certain planets are in a particular astrological configuration. The end-user 102 may consult the "Dosing" topic for information on dosing under various conditions, and she may peruse sources for acquisition to select a mode of purchase, to conclude the purchase, and to arrange for delivery.

Figure 7:
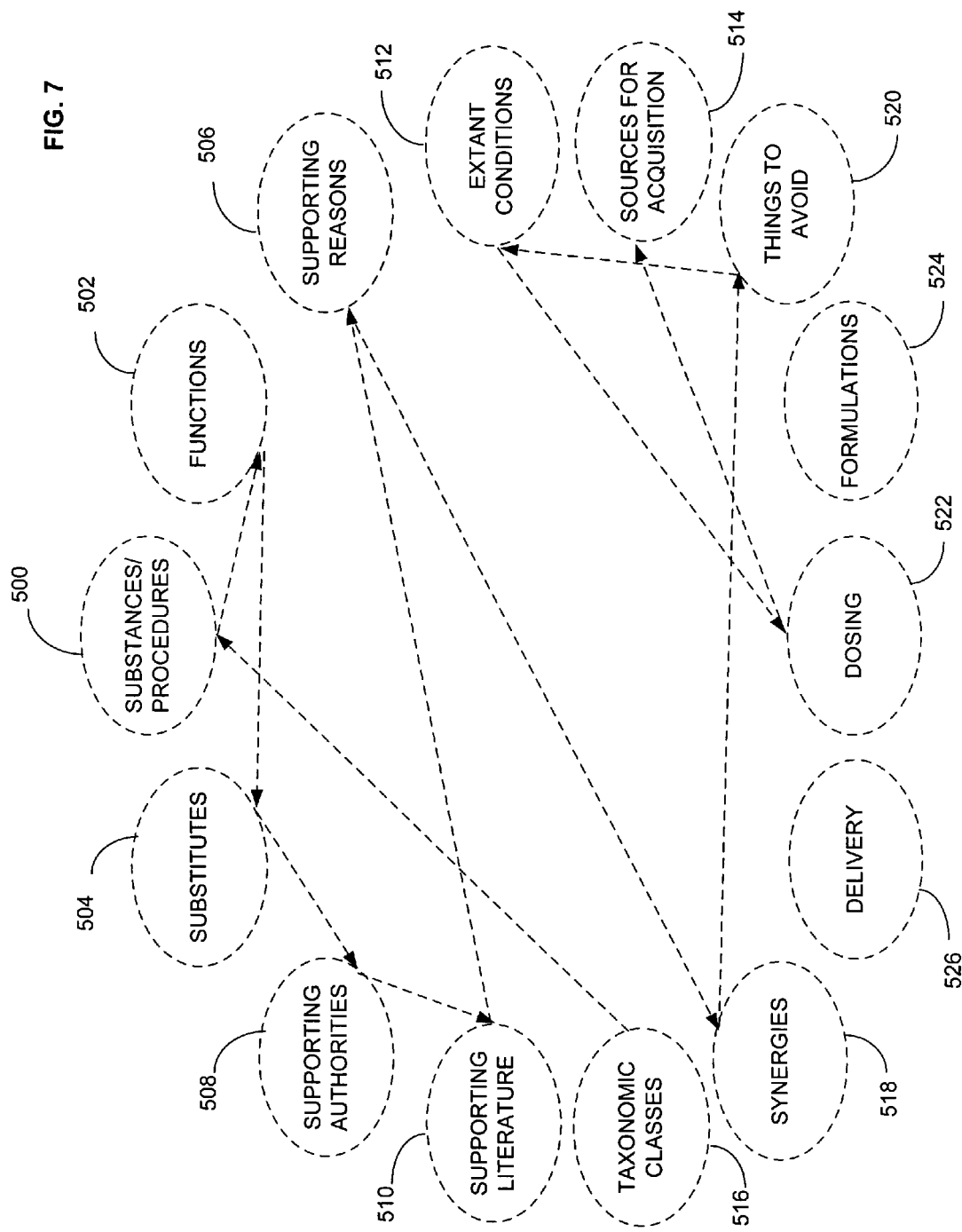
FIG. 7 depicts an alternative exemplary view of the aspects of the embodiment depicted in FIG. 6.

FIG. 7 depicts an alternative exemplary way to view the pathway of an end-user 102 through data in the data structure depicted in FIG. 6, using as a template the depiction of FIG. 5.

Figure 8:
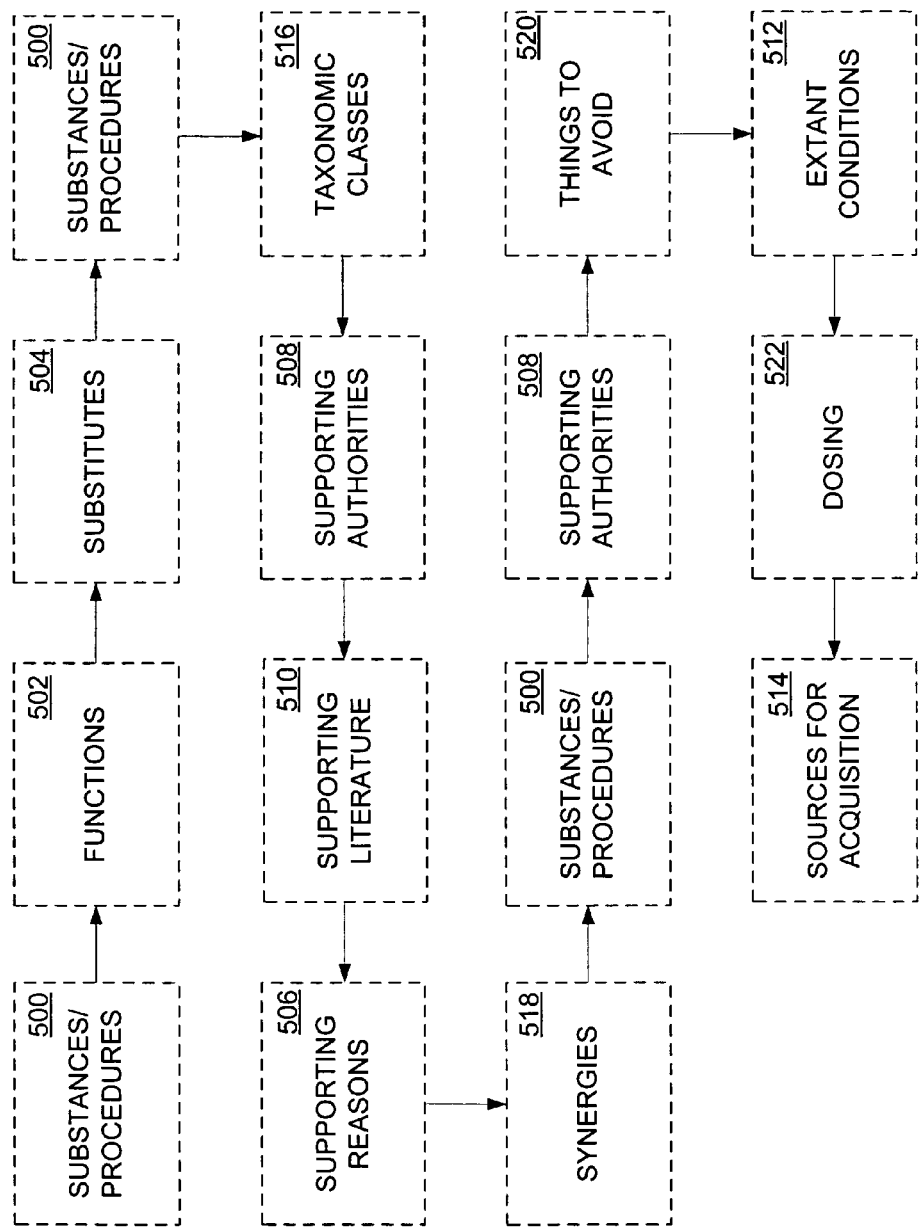
FIG. 8 depicts an exemplary view of aspects of an embodiment.

FIG. 8 depicts an exemplary view of the pathway of an end-user 102 through data in the data structure. The end-user 102 starts with a substance, e.g., Substance M, and looks up functions for Substance M, e.g., protection against cancer. The end-user 102 then looks up substitutes for Substance M for protection against cancer, e.g., Substance N. The end-user 102 then becomes interested in Substance N for other purposes. Going back to the topic "Substances/Procedures" to learn about Substance N, the end-user 102 learns that Substance N is a member of a particular taxonomic class, e.g. acids. The end-user 102 reassures himself of the efficacy of Substance N for some other purpose, e.g., prevention of hair loss, by consulting a supporting authority, e.g., a famous cancer researcher, supporting literature, e.g., a *Scientific American* article, and supporting reasons, e.g., a published explanation of why Substance N prevents hair loss. The end-user 102 retrieves information on synergies from the use of Substance N and Substance O, e.g., enhanced prevention of hair loss and fresher breath, and on things to avoid, e.g., the use of Substance N with, e.g., Substance P, which would lead to decreased efficacy for hair loss and extensive skin rashes. The end-user 102 calls up the effects of extant conditions on the use of Substance N, e.g., amplification of any already-present schizophrenia when certain planets are in a particular astrological configuration. The end-user 102 finishes by retrieving dosing information and proceeding to purchase through a source for acquisition.

Figure 9:
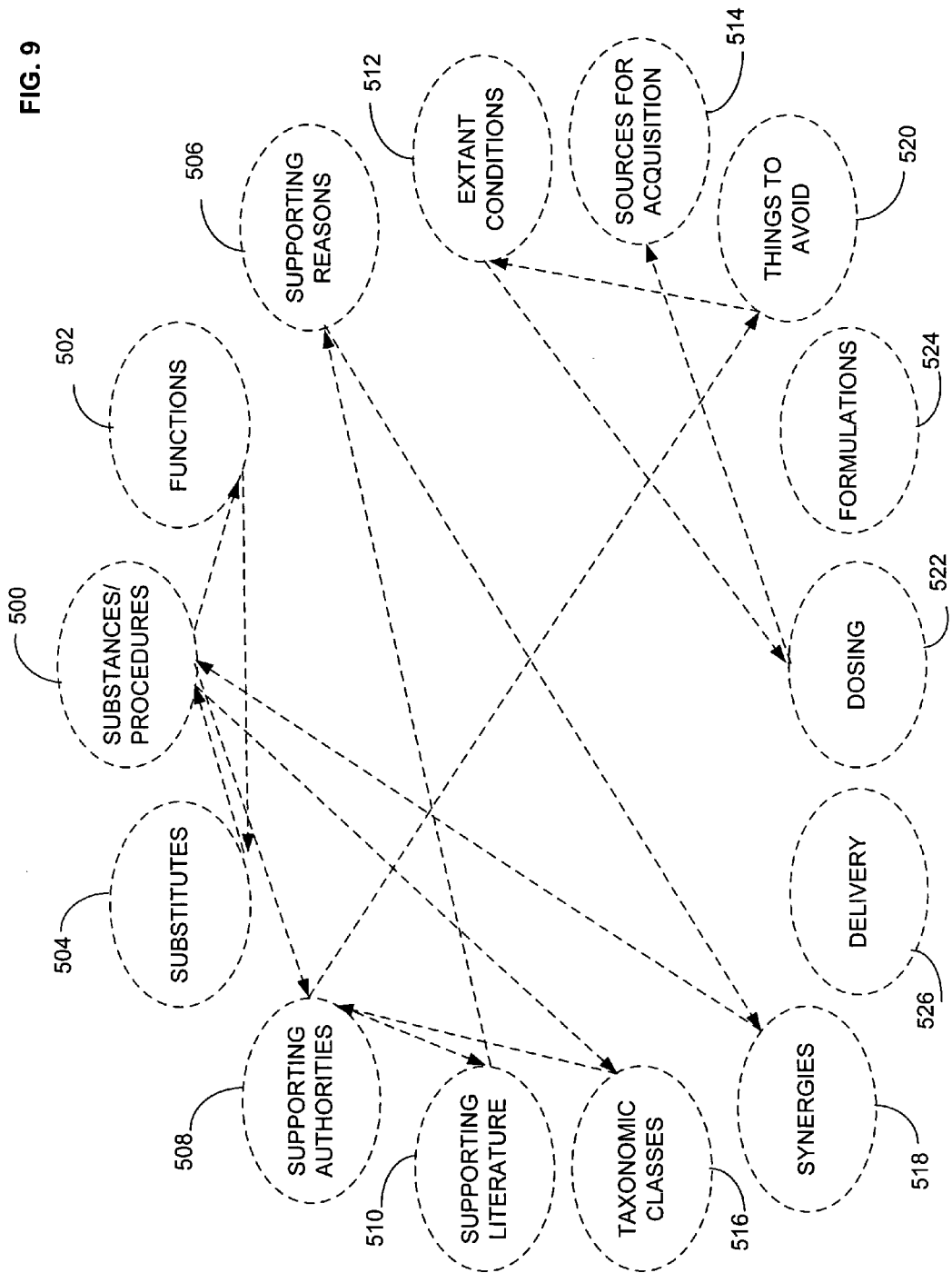
FIG. 9 depicts an alternative exemplary view of the aspects of the embodiment depicted in FIG. 8.

FIG. 9 depicts an alternative exemplary way to view the pathway of an end-user 102 through data in the data structure depicted in FIG. 8, using as a template the depiction of FIG. 5.

Figure 10:
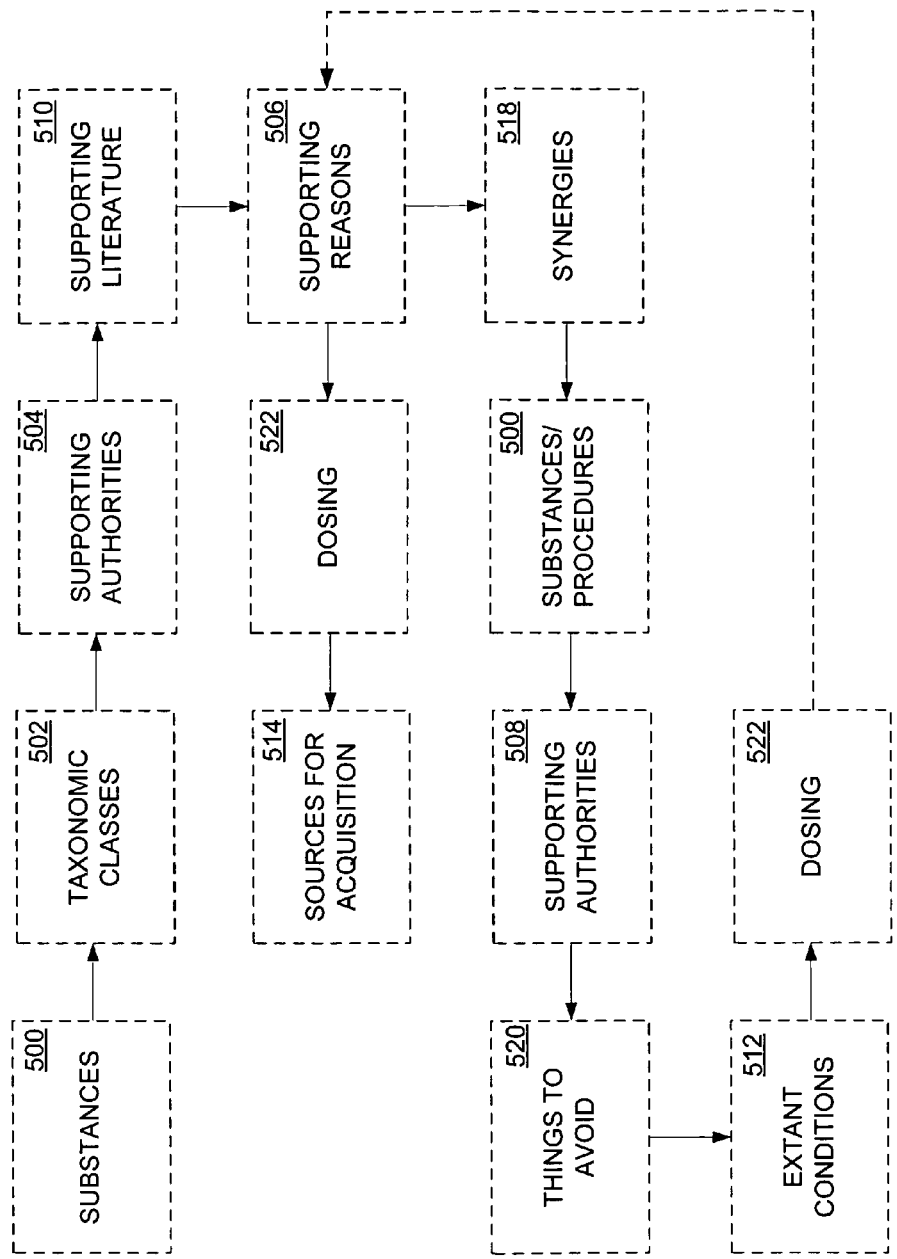
FIG. 10 depicts an exemplary view of aspects of an embodiment.

FIG. 10 depicts an exemplary way to view a branched pathway of an end-user 102 through data in the data structure. The end-user starts with a substance, e.g., Substance P, and looks up taxonomic classes associated with for Substance P, e.g., water soluble vitamins. The end-user 102 then looks up supporting authorities for the use of water soluble vitamins for protection against cancer, such as a columnist in a well-known health magazine, and moves on to supporting literature, e.g., articles in reference journals, and supporting reasons, e.g., explanations of the functionality of water soluble vitamins for prevention of cancer. At this point, the end-user 102 remembers that a friend had been asking about the use of water soluble vitamins for other purposes, such as prevention of hair loss, especially in combination with certain procedures for their use. Leaving aside his original search, the end-user 102 takes up his friend's question and looks up synergies with regard to water soluble vitamins. After perusing synergies, he selects a procedure, e.g., taking a particular water soluble vitamin in conjunction with a food such as a particular fruit. He looks up supporting authorities for the efficacy of the water soluble vitamin in conjunction with the fruit for preventing hair loss, e.g., a medical society. He then checks for things to avoid, such as the use of a second vitamin that would reduce the effectiveness of the first vitamin and the fruit, and extant conditions, such as humidity, which might affect the usefulness of the water soluble vitamin. Finally, he looks at the appropriate dosing for the water soluble vitamin. Having investigated his friend's question, he returns to his original search. He had been looking up supporting reasons for the use of water soluble vitamins to prevent cancer. He resumes his research at that point and moves on to investigate appropriate dosing. Finally, he moves to sources for acquisition of the Substance P.

Figure 11:
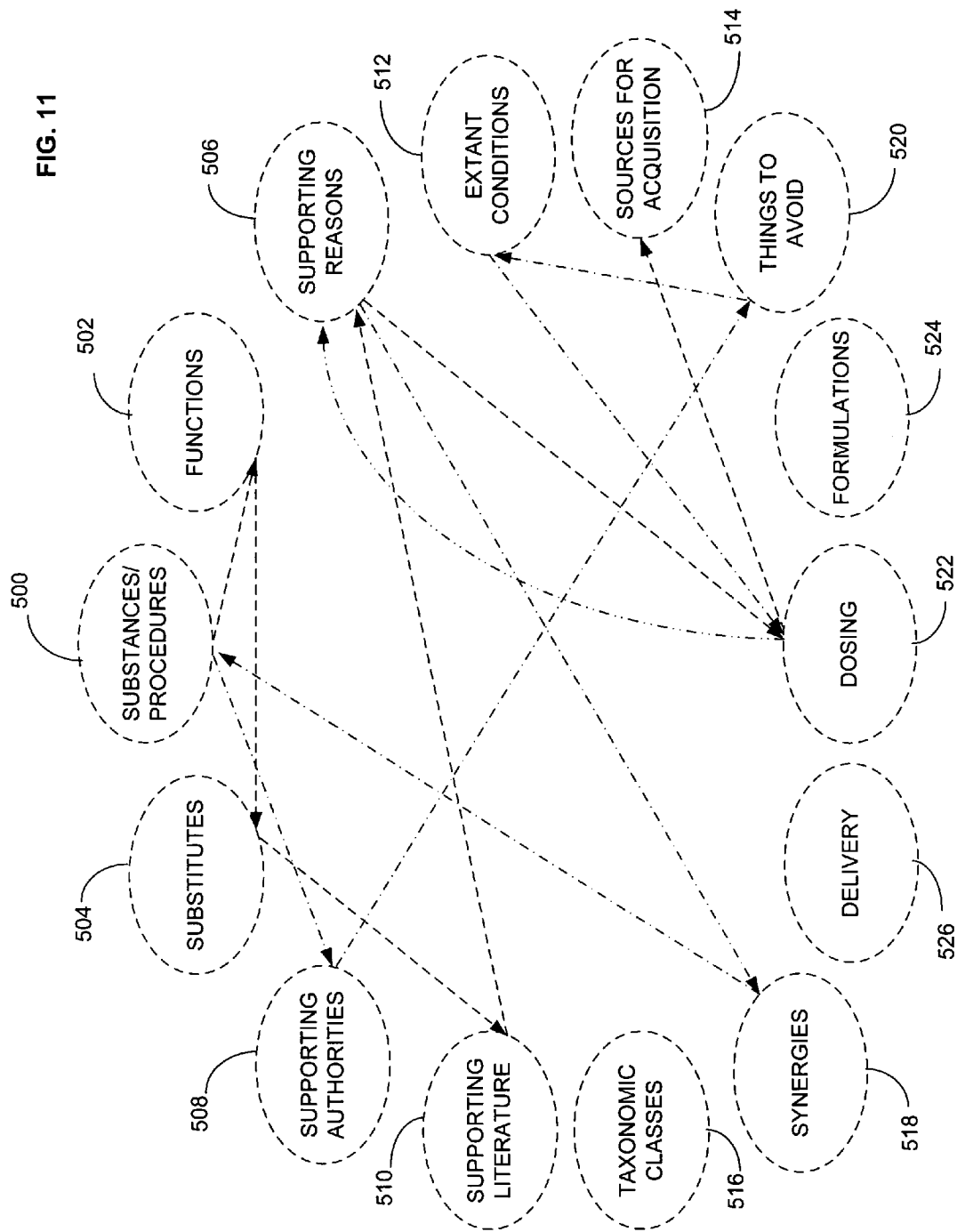
FIG. 11 depicts an alternative exemplary view of aspects of the embodiment depicted in FIG. 10.

FIG. 11 depicts an alternative exemplary way to view the pathway of an end-user 102 through data in the data structure depicted in FIG. 10, using as a template the depiction of FIG. 5.

The end-user 102 may search the data structure for patterns, finding correlations between health regimen data entities that would otherwise not be discoverable or that would be very difficult to discover. For example, the end-user 102 may search for effects of Substance A on skin rashes in conditions of high humidity, searching, among other health regimen data entities, those including anecdotal evidence from users of Substance A in high humidity, where the users of Substance A also had skin rashes and reported apparent effects of Substance A on those rashes. Such searches for correlations may include information and observations added to the data structure by all or any of the end-users 102, vendors 108, and/or publishers 112 using the data structure. Such searches may be used to test hypotheses about the efficacy and safety of pharmaceutical, nutraceutical, veterinary, dietary, and/or nutritional substances, procedures, processes, and/or practices of interest.

As mentioned above, end-users 102 may add health regimen data entities to the data structure to report experiences with the use of substances/procedures. For example, an end-user 102 may integrate a report of an experience, e.g., partial success with the use of Substance B for reduction of hair loss in low-humidity conditions but little success in conditions of high-humidity, by selecting pre-existing health regimen data entities with which to associate new health regimen data entities that represent relevant elements of his report, and/or by associating new health regimen data entities that represent relevant elements of his report with pre-existing annotations to pre-existing health regimen data entities added by other end-users 102 with similar reports. An end-user 102 may also add health regimen data entities representing the results of correlative searches such as those described above, e.g., by adding health regimen data entities representing the results of such a search and associating them with pre-existing health regimen data entities associated with, e.g., a Substance C used to alleviate heartburn in connection with particular dietary conditions.

In using the data structure, the end-user 102 may impose his own schema on the information searched and on the output of the search. The end-user 102 may explicitly include or exclude for search purposes health regimen data entities representing factors such as weather information or astrological information. He may include or exclude for search results reporting purposes various complexities, e.g., including tables of correlations for further study, but excluding such information and including only lists of ingredients and instructions for purposes of making a particular substance for use or lists of dosages to serve as input into medical dispensing devices, either indirectly through human input to devices or automatically through direct input of dosage information to devices.

Figure 12:
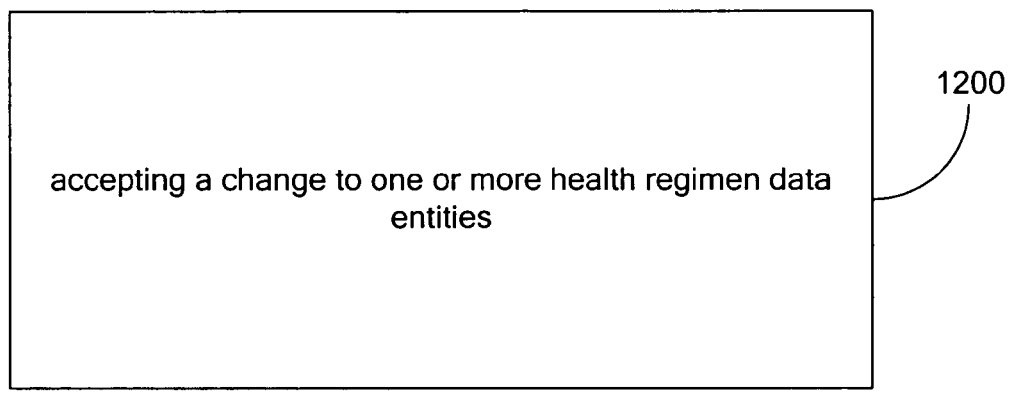
FIG. 12 depicts a high-level logic flowchart of an operational process.

FIG. 12 depicts a high-level logic flowchart of an operational process. Operation 1200 shows accepting a change to one or more health regimen data entities (e.g., accepting an addition and/or a deletion and/or an alteration of a health regimen data entity such as a health regimen data entity 312 comprising a personal note of the effect of taking a substance, where the addition and/or deletion and/or alteration of the health regimen data entity 312 is performed by the end-user 102 to a data structure/data structures (e.g., which may be distributed data structures) stored at least in part on a computer such as computer 104, using the hardware/software/firmware of computer 104).

Figure 13A:
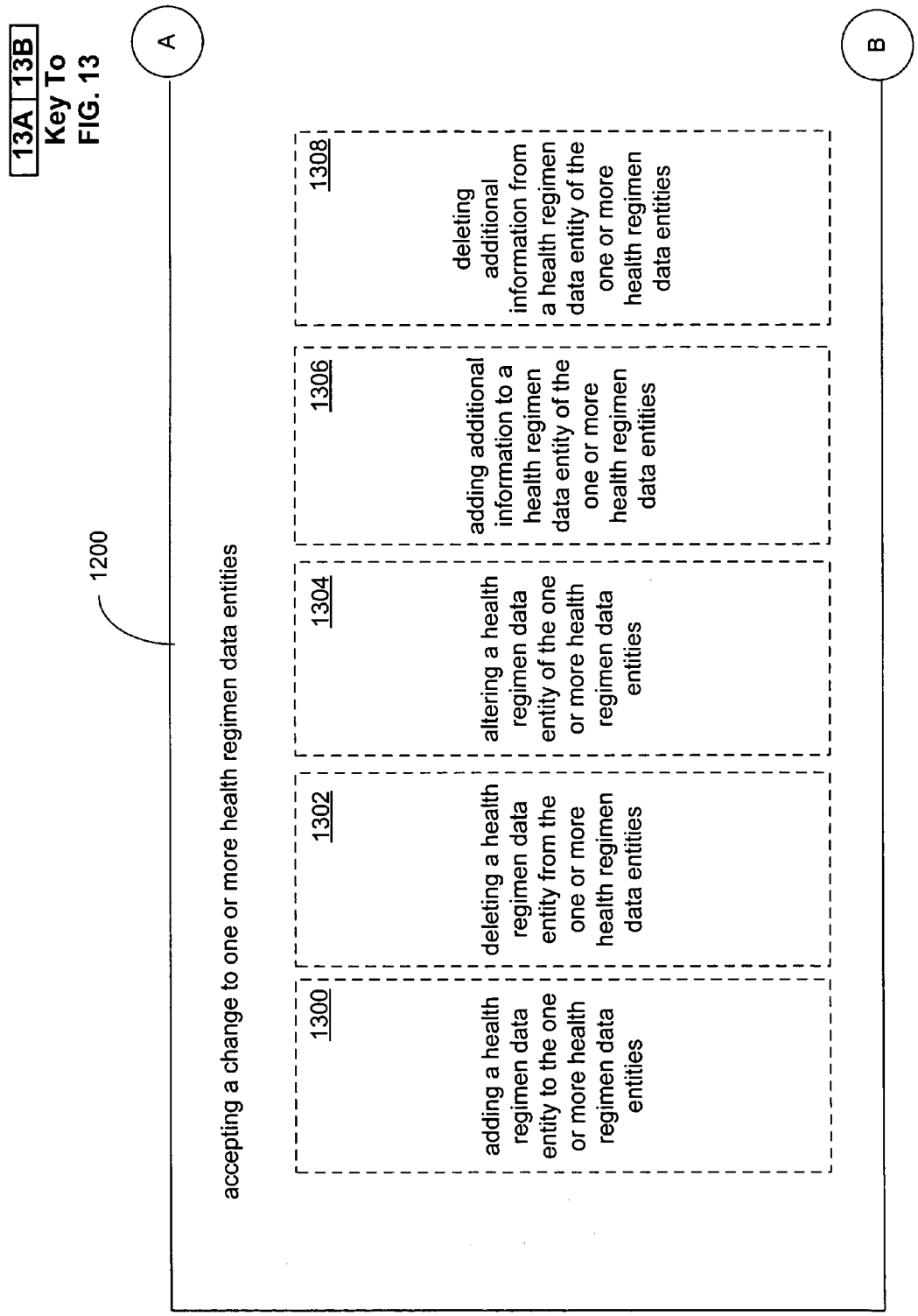
FIG. 13 shows several alternative implementations of the high-level logic flowchart of FIG. 12.
Figure 13B:
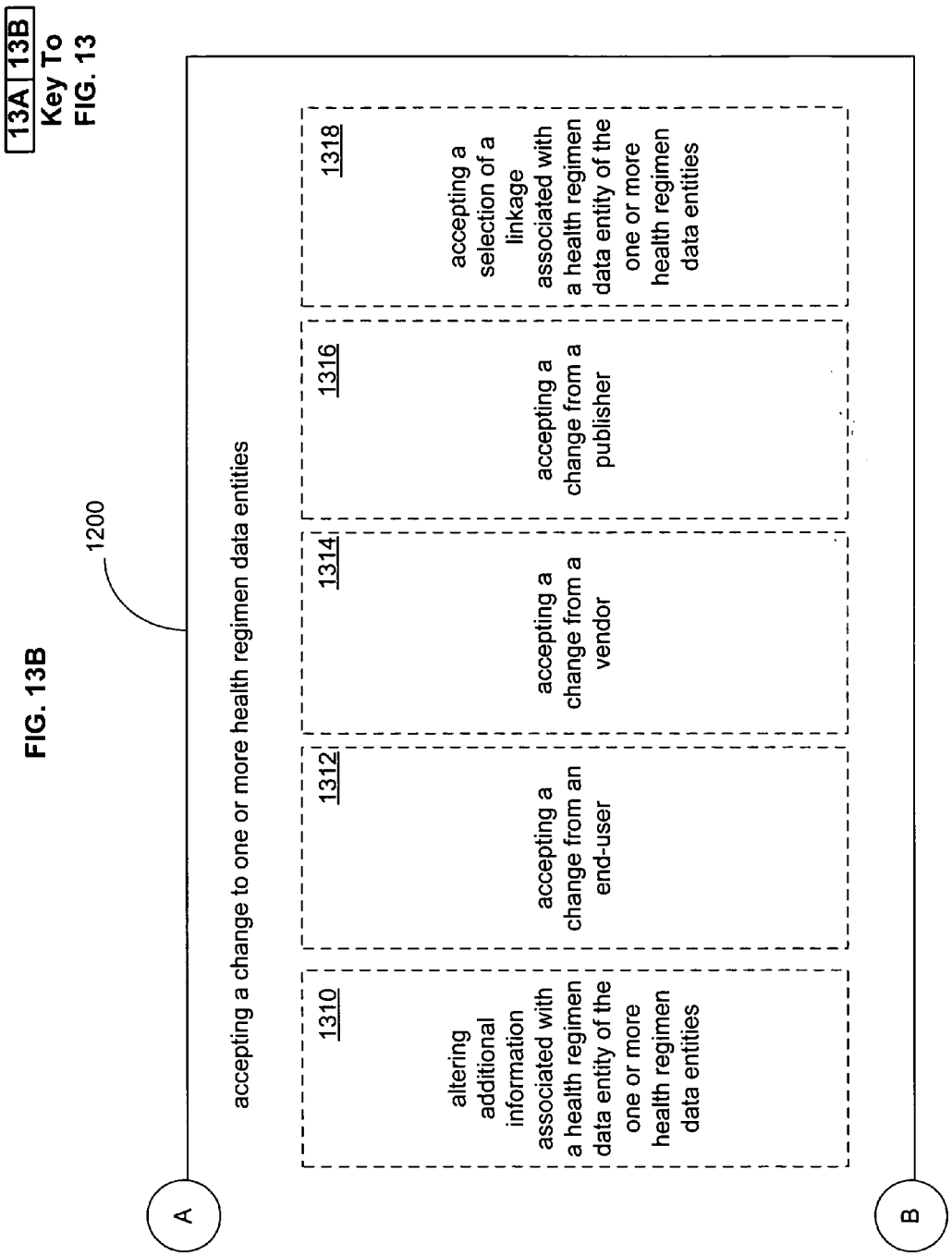

FIG. 13 shows several alternative implementations of the high-level logic flowchart of FIG. 12. Operation 1200—accepting a change to one or more health regimen data entities—may include one or more of the following operations: 1300, 1302, 1304, 1306, 1308, 1310, 1312, 1314, 1316, and/or 1318. Operation 1300 depicts adding a health regimen data entity to the one or more health regimen data entities (e.g., adding a health regimen data entity such as a personal note 312 of an effect of taking a substance, where the adding is performed by the end-user 102 to a data structure/data structures (e.g., which may be distributed data structures) stored at least in part on a computer such as computer 104, using the hardware/software/firmware of computer 104). Operation 1302 shows deleting a health regimen data entity from the one or more health regimen data entities (e.g., deleting a health regimen data entity such as a vitamin regimen 400, where the deleting is performed by the vendor 108 from a data structure/data structures (e.g., which may be distributed data structures) stored at least in part on a computer such as computer 110, using the hardware/software/firmware of computer 110; it should be understood, irrespective of the foregoing example, that the adding and/or deleting and/or altering described herein may be performed by any party—e.g. deleting would not be limited to the party recited). Operation 1304 illustrates altering a health regimen data entity of the one or more health regimen data entities (e.g., altering a health regimen data entity, such as a vitamin regimen 408, where the altering is performed by the publisher 112 on a health regimen data entity that is part of a data structure/data structures (e.g., which may be distributed data structures) stored at least in part on a computer 114, using the hardware/software/firmware of computer 114). Operation 1306 depicts adding additional information to a health regimen data entity of the one or more health regimen data entities (e.g., adding additional information, such as cautions regarding the use of nutraceutical substance, to a health regimen data entity 206, where the adding is performed by the publisher 112 to a health regimen data entity that is part of a data structure/data structures (e.g., which may be distributed data structures) that is at least in part stored on computer 114, using the hardware/software/firmware of computer 114; additionally, e.g., adding additional information such as that listed in association with any of the health regimen data entities 208, and/or 212). Operation 1308 illustrates deleting additional information from a health regimen data entity of the one or more health regimen data entities (e.g., deleting additional information such as a link to a research paper, from a health regimen data entity 206, where the deleting is performed by the vendor 108 to a health regimen data entity that is part of a data structure/data structures (e.g., which may be distributed data structures) stored at least in part on computer 110, using the hardware/software/firmware of computer 110). Operation 1310 shows altering additional information associated with a health regimen data entity of the one or more health regimen data entities (e.g., altering additional information such as caution information associated with a health regimen data entity that is part of a data structure/data structures (e.g., which may be distributed data structures) stored at least in part on computer 104, where the altering is performed by the end-user 102, using the hardware/software/firmware of computer 104). Operation 1312 illustrates accepting a change from an end-user (e.g., accepting a change from an end-user 102, such as an addition of a personal note as a health regimen data entity 312, to a data structure/data structures (e.g., which may be distributed data structures) stored at least in part on a computer such as computer 104, using the hardware/software/firmware of computer 104). Operation 1314 shows accepting a change from a vendor (e.g., accepting a change from a vendor 108, such as an addition of a substance dosage as a health regimen data entity 402, to a data structure/data structures (e.g., which may be distributed data structures) stored at least in part on a computer such as computer 110, using the hardware/software/firmware of computer 110). Operation 1316 depicts accepting a change from a publisher (e.g., accepting a change from a publisher 112, such as an addition of a link 308 to a usage report health regimen data entity 312, to a data structure/data structures (e.g., which may be distributed data structures) stored at least in part on a computer such as computer 114, using the hardware/software/firmware of computer 114). Operation 1318 illustrates accepting a selection of a linkage associated with a health regimen data entity of the one or more health regimen data entities (e.g., accepting a linkage from an end-user 102 and/or a vendor 108 and/or a publisher 112, such as a linkage 310 from a personal note 312 regarding a substance usage to a health regimen data entity 304 comprising an identifier for lithium, in a data structure/data structures (e.g., which may be distributed data structures) stored at least in part on computer 104 and/or computer 110 and/or computer 114, using the hardware/software/firmware of computer 104 and/or computer 110 and/or computer 114; additionally, e.g., accepting any of the linkages 216, 302, 308, 418, and/or 424). Although some of the examples herein involve health regimen data entities, it should be understood that one terminus of a linkage may be an item that is different from a health regimen data entity; such examples are not expressly included herein for the sake of clarity.

FIG. 14 shows several alternative implementations of the high-level logic flowchart of FIG. 13. Operation 1318—accepting a selection of a linkage associated with a health regimen data entity of the one or more health regimen data entities—may include one or more of the following operations: 1400, 1402, 1404, 1406, 1408, 1410, 1412, 1414, and/or 1416. Operation 1400 shows accepting a selection of a health regimen data entity associated with the linkage (e.g., accepting a selection of a health regimen data entity, such as a health regimen data entity 304 comprising an identifier for lithium, associated with a linkage 310, where the selection is accepted from an end-user 102, and where the health regimen data entity 304 and the linkage 310 are part of a data structure/data structures (e.g., which may be distributed data structures) that is stored at least in part on computer 104, using the hardware/software/firmware of computer 104). Operation 1402 depicts accepting a linkage from a first nesting health regimen data entity to a second nesting health regimen data entity (e.g., accepting a linkage 418 from a health regimen data entity, such as personal notes about usage 306, to another health regimen data entity, such as Brand Y vitamin regimen 408, where the linkage is accepted from an end-user 102, and where the health regimen data entities 306 and 408 and the linkage 418 are part of a data structure/data structures (e.g., which may be distributed data structures) that is stored at least in part on computer 104, using the hardware/software/firmware of computer 104; additionally, e.g., accepting a linkage to and/or from nesting health regimen data entities 204, 210, 212, 400, and/or 410). Operation 1404 illustrates accepting a linkage from a nesting health regimen data entity to a nested health regimen data entity (e.g., accepting a linkage from a nesting health regimen data entity such as an identifier for lithium 204 to a nested health regimen data entity 206 comprising indications, cautions, and research associated with lithium, where the linkage is accepted from a publisher 112, and where the linkage and the health regimen data entities 204 and 204 are parts of a data structure/data structures (e.g., which may be distributed data structures) stored at least in part on the computer 114, using the hardware/software/firmware of computer 114; additionally, e.g., accepting a linkage to any of the nested health regimen data entities 208, 212, 214, 220, 312, 314, 402, 404, 406, 410, 412, 414, and/or 416). Operation 1406 illustrates accepting a linkage from a first nested health regimen data entity to a second nested health regimen data entity (e.g., accepting a linkage 428 from a nested health regimen data entity 314 such as a personal note regarding usage of a substance, to another health regimen data entity 416 such as a constituent in a vitamin regimen, where the linkage 428 is accepted from an end-user 102, and where the linkage 428 and health regimen data entities 314 and 416 are parts of a data structure/data structures (e.g., which may be distributed data structures) stored at least in part on the computer 104, using the hardware/software/firmware of computer 104; additionally, e.g., accepting the linkage 426 from the nested health regimen data entity 406 to the nested health regimen data entity 404). Operation 1408 depicts accepting a linkage from a nested health regimen data entity to a nesting health regimen data entity (e.g., accepting a linkage 430 from a nested health regimen data entity 314 such as a personal note regarding usage of a substance, to another health regimen data entity 408 such as a vitamin regimen, where the linkage 430 is accepted from a vendor 108, and where the linkage 430 and the health regimen data entities 314 and 408 are parts of a data structure/data structures (e.g., which may be distributed data structures) stored at least in part on computer 110, using the using the hardware/software/firmware of computer 110; additionally, e.g., accepting a linkage that is implicit in the relationship between a nested health regimen data entity 402 to a nesting health regimen data entity 400 within which it is nested). Operation 1410 depicts accepting a linkage from a nesting health regimen data entity to a non-nesting health regimen data entity (e.g., accepting a linkage 216 from a nesting health regimen data entity 212 comprising indications, cautions, and research information associated with lithium, to a non-nesting health regimen data entity 218 comprising an identifier for lithium, where the linkage 216 is accepted from a publisher 112, and where the linkage 216 and health regimen data entities 212 and 218 are parts of a data structure/data structures (e.g., which may be distributed data structures) stored at least in part on the computer 114, using the hardware/software/firmware of computer 114; additionally, e.g., accepting a linkage to any non-nesting health regimen data entity 202, 206, 208, 214, 220, 300, 304, 312, 314, 402, 404, 406, 412, 414, 416, 420, and/or 422; additionally, e.g., accepting a linkage implicit in the relationship between a nesting health regimen data entity 400 and any non-nesting health regimen data entity 402 that is nested within the nesting health regimen data entity). Operation 1412 shows accepting a linkage from a nesting health regimen data entity to a non-nested health regimen data entity (e.g., accepting a linkage 418 from a nesting health regimen data entity 408 comprising a Brand Y vitamin regimen to another health regimen data entity 306 comprising personal notes regarding the usage of lithium, where the linkage 418 is accepted from a vendor 108, and where the linkage 418 and health regimen data entities 408 and 306 are parts of a data structure/data structures (e.g., which may be distributed data structures) stored at least in part on the computer 110, using the hardware/software/firmware of computer 110; additionally, e.g., accepting a linage to any non-nested health regimen data entity 202, 204, 210, 218, 300, 304, 400, 408, 420, and/or 422, such as linkage 216). Operation 1414 depicts accepting a linkage from a nested health regimen data entity to a non-nesting health regimen data entity (e.g., accepting a linkage from a nested health regimen data entity 212 comprising indications, cautions, and research associated with lithium, to another health regimen data entity 214 comprising the indication of depression, where the linkage is accepted from an end-user 102, and where the linkage and health regimen data entities 212 and 214 are parts of a data structure/data structures (e.g., which may be distributed data structures) stored at least in part on the computer 104, using the hardware/software/firmware of computer 104; additionally, e.g., accepting a linkage 216 from the nested health regimen data entity 212 to the non-nesting health regimen data entity 218). Operation 1416 depicts accepting a linkage from a nested health regimen data entity to a non-nested health regimen data entity (e.g., accepting a linkage 310 from a nested health regimen data entity 312 comprising a personal note regarding the usage of lithium, to another health regimen data entity 304 comprising an identifier for lithium, where the linkage 310 is accepted from an end-user 102, and where the linkage 310 and health regimen data entities 304 and 312 are parts of a data structure/data structures (e.g., which may be distributed data structures) stored at least in part on the computer 104, using the hardware/software/firmware of computer 104).

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment).

Those skilled in the art will recognize that it is common within the art to describe devices and/or processes in the fashion set forth herein, and thereafter use engineering practices to integrate such described devices and/or processes into image processing systems. That is, at least a portion of the devices and/or processes described herein can be integrated into an image processing system via a reasonable amount of experimentation. Those having skill in the art will recognize that a typical image processing system generally includes one or more of a system unit housing, a video display device, a memory such as volatile and non-volatile memory, processors such as microprocessors and digital signal processors, computational entities such as operating systems, drivers, and applications programs, one or more interaction devices, such as a touch pad or screen, control systems including feedback loops and control motors (e.g., feedback for sensing lens position and/or velocity; control motors for moving/distorting lenses to give desired focuses. A typical image processing system may be implemented utilizing any suitable commercially available components, such as those typically found in digital still systems and/or digital motion systems.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

All of the above U.S. patents, U.S. patent application publications, U.S. patent applications, foreign patents, foreign patent applications and non-patent publications referred to in this specification and/or listed in any Application Data Sheet, are incorporated herein by reference, in their entireties.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of this subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

We claim:

1. A method for a computer processor related to health-related data management, the method comprising:

controlling at least one network health regimen information database at least partially using one or more processing components including at least:
providing health regimen information in the at least one network health regimen information database including one or more data structures linked by associative information;
enabling a plurality of users of the at least one network health regimen information database at least to access, add, and modify information in the at least one network health regimen information database including at least enabling the plurality of users to modify one or more linkages between health regimen entities;
accepting input information from at least one user of the plurality of users of the at least one network health regimen information database, the input information including at least information indicating at least one of patterns or correlations between health regimen entities in the health regimen information linked by associative information;
automatically correlating one or more health regimen entities including adding associative information to the one or more data structures including at least one of pointers or identifiers indicating at least one or more linkages between two or more health regimen data entities based at least partly on the information indicating at least one of patterns or correlations between health regimen entities in the health regimen information linked by associative information and user modification of the one or more linkages between health regimen entities; and
storing the associative information to the one or more data structures including at least one of pointers or identifiers indicating at least one or more linkages between the two or more health regimen data entities, wherein accessibility to the health regimen entities in the at least one network health regimen information database is modified in response to the input information received from the at least one user.

2. The method of claim 1, wherein the accepting input information from at least one user of the plurality of users of the at least one network health regimen information database includes:
at least one of:
accepting input information for changing one or more health regimen data entities; or
accepting input information for altering one or more health regimen data entities.

3. The method of claim 1, wherein the accepting input information from at least one user of the plurality of users of the at least one network health regimen information database includes:
accepting input information for deleting one or more health regimen data entities.

4. The method of claim 1, wherein the accepting input information from at least one user of the plurality of users of the at least one network health regimen information database includes:
accepting input information for including at least one table of correlation in one or more data structures.

5. The method of claim 1, wherein the accepting input information from at least one user of the plurality of users of the at least one network health regimen information database includes:
accepting input information for adding information to one or more health regimen data entities.

6. The method of claim 1, wherein the accepting input information from at least one user of the plurality of users of the at least one network health regimen information database includes:
accepting input information for deleting information from one or more health regimen data entities.

7. The method of claim 1, wherein the accepting input information from at least one user of the plurality of users of the at least one network health regimen information database includes:
accepting input information for integrating at least one report of an experience by at least one end-user into one or more health regimen data entities.

8. The method of claim 1, wherein the accepting input information from at least one user of the plurality of users of the at least one network health regimen information database includes:
accepting input information for accepting a change in one or more health regimen data entities from an end-user.

9. The method of claim 1, wherein the accepting input information from at least one user of the plurality of users of the at least one network health regimen information database includes:
accepting input information for accepting a change in one or more health regimen data entities from a vendor.

10. The method of claim 1, wherein the accepting input information from at least one user of the plurality of users of the at least one network health regimen information database includes:
at least one of:
accepting input information for accepting a change in one or more health regimen data entities from a publisher; or
accepting input information for accepting a selection of at least one health regimen data entity.

11. The method of claim 1, wherein the plurality of users of the at least one network health regimen information database includes:
at least one of an end-user, a vendor, or a publisher.

12. The method of claim 1, wherein the automatically correlating one or more health regimen entities including adding associative information to the one or more data structures including at least one of pointers or identifiers indicating at least one or more linkages between two or more health regimen data entities comprises:
automatically correlating one or more health regimen entities including adding associative information to the one or more data structures including at least one of pointers or identifiers indicating at least one or more linkages between a first nesting health regimen data entity and a second nesting health regimen data entity that is linked with one or more other health regimen data entities.

13. The method of claim 1, wherein the automatically correlating one or more health regimen entities including adding associative information to the one or more data structures including at least one of pointers or identifiers indicating at least one or more linkages between two or more health regimen data entities comprises:
automatically correlating one or more health regimen entities including adding associative information to the one or more data structures including at least one of pointers or identifiers indicating at least one or more linkages between a first nesting health regimen data entity and a second nested health regimen data entity that is linked with one or more other health regimen data entities.

14. The method of claim 1, wherein the automatically correlating one or more health regimen entities including adding associative information to the one or more data structures including at least one of pointers or identifiers indicating at least one or more linkages between two or more health regimen data entities comprises:
automatically correlating one or more health regimen entities including adding associative information to the one or more data structures including at least one of pointers or identifiers indicating at least one or more linkages between a first nested health regimen data entity and a second nested health regimen data entity that is linked with one or more other health regimen data entities.

15. The method of claim 1, wherein the automatically correlating one or more health regimen entities including adding associative information to the one or more data structures including at least one of pointers or identifiers indicating at least one or more linkages between two or more health regimen data entities comprises:
automatically correlating one or more health regimen entities including adding associative information to the one or more data structures including at least one of pointers or identifiers indicating at least one or more linkages between a first nested health regimen data entity and a second nesting health regimen data entity that is linked with one or more other health regimen data entities.

16. The method of claim 1, wherein the automatically correlating one or more health regimen entities including adding associative information to the one or more data structures including at least one of pointers or identifiers indicating at least one or more linkages between two or more health regimen data entities comprises:

automatically correlating one or more health regimen entities including adding associative information to the one or more data structures including at least one of pointers or identifiers indicating at least one or more linkages between a first nesting health regimen data entity and a second non-nesting health regimen data entity that is linked with one or more other health regimen data entities.

17. The method of claim 1, wherein the automatically correlating one or more health regimen entities including adding associative information to the one or more data structures including at least one of pointers or identifiers indicating at least one or more linkages between two or more health regimen data entities comprises:

automatically correlating one or more health regimen entities including adding associative information to the one or more data structures including at least one of pointers or identifiers indicating at least one or more linkages between a first nesting health regimen data entity and a second non-nested health regimen data entity that is linked with one or more other health regimen data entities.

18. The method of claim 1, wherein the automatically correlating one or more health regimen entities including adding associative information to the one or more data structures including at least one of pointers or identifiers indicating at least one or more linkages between two or more health regimen data entities comprises:

automatically correlating one or more health regimen entities including adding associative information to the one or more data structures including at least one of pointers or identifiers indicating at least one or more linkages between a first nested health regimen data entity and a second non-nesting health regimen data entity that is linked with one or more other health regimen data entities.

19. The method of claim 1, wherein the automatically correlating one or more health regimen entities including adding associative information to the one or more data structures including at least one of pointers or identifiers indicating at least one or more linkages between two or more health regimen data entities comprises:

automatically correlating one or more health regimen entities including adding associative information to the one or more data structures including at least one of pointers or identifiers indicating at least one or more linkages between a first nested health regimen data entity and a second non-nested health regimen data entity that is linked with one or more other health regimen data entities.

20. The method of claim 1, wherein the automatically correlating one or more health regimen entities including adding associative information to the one or more data structures including at least one of pointers or identifiers indicating at least one or more linkages between two or more health regimen data entities comprises:

automatically correlating one or more health regimen entities including adding associative information to the one or more data structures including at least one of pointers or identifiers indicating at least one or more linkages between a vitamin regimen data entity and a constituent substance data entity that is linked with one or more personal notes data entities.

21. The method of claim 1, wherein the automatically correlating one or more health regimen entities including adding associative information to the one or more data structures including at least one of pointers or identifiers indicating at least one or more linkages between two or more health regimen data entities comprises:

automatically correlating one or more health regimen entities including adding associative information to the one or more data structures including at least one of pointers or identifiers indicating at least one or more linkages between a vitamin regimen data entity and a constituent substance data entity that is linked with one or more personal notes data entities.

22. A system comprising:

at least one server configured for controlling at least one network health regimen information database at least partially using one or more processing components including at least:

at least one memory configured for storing health regimen information in the at least one network health regimen information database including one or more data structures linked by associative information;

circuitry configured for enabling a plurality of users of the at least one network health regimen information database at least to access, add, and modify information in the at least one network health regimen information database including at least enabling the plurality of users to modify one or more linkages between health regimen entities;

circuitry configured for accepting input information from at least one user of the plurality of users of the at least one network health regimen information database, the input information including at least information indicating at least one of patterns or correlations between health regimen entities in the health regimen information linked by associative information;

circuitry configured for automatically correlating one or more health regimen entities including adding associative information to the one or more data structures including at least one of pointers or identifiers indicating at least one or more linkages between two or more health regimen data entities based at least partly on the information indicating at least one of patterns or correlations between health regimen entities in the health regimen information linked by associative information and user modification of the one or more linkages between health regimen entities; and circuitry configured for storing the associative information to the one or more data structures including at least one of pointers or identifiers indicating at least one or more linkages between the two or more health regimen data entities, wherein accessibility to the health regimen entities in the at least one network health regimen information database is modified in response to the input information received from the at least one user.

23. A system comprising:

means for controlling at least one network health regimen information database at least partially using one or more non-transitory computer readable media bearing one or more instructions executable on one or more processing components including at least:

means for providing health regimen information in the at least one network health regimen information database including one or more data structures linked by associative information;

means for enabling a plurality of users of the at least one network health regimen information database at least to access, add, and modify information in the at least one network health regimen information database including at least enabling the plurality of users to modify one or more linkages between health regimen entities;

means for accepting input information from at least one user of the plurality of users of the at least one network health regimen information database, the input information including at least information indicating at least one of patterns or correlations between health regimen entities in the health regimen information linked by associative information;

means for automatically correlating one or more health regimen entities including adding associative information to the one or more data structures including at least one of pointers or identifiers indicating at least one or more linkages between two or more health regimen data entities based at least partly on the information indicating at least one of patterns or correlations between health regimen entities in the health regimen information linked by associative information and user modification of the one or more linkages between health regimen entities; and means for storing the associative information to the one or more data structures including at least one of pointers or identifiers indicating at least one or more linkages between the two or more health regimen data entities, wherein accessibility to the health regimen entities in the at least one network health regimen information database is modified in response to the input information received from the at least one user.

24. A system comprising:
one or more non-transitory computer readable media bearing one or more instructions for facilitating operations including at least:
controlling at least one network health regimen information database at least partially using one or more processing components including at least:
providing health regimen information in the at least one network health regimen information database including one or more data structures linked by associative information;
enabling a plurality of users of the at least one network health regimen information database at least to access, add, and modify information in the at least one network health regimen information database including at least enabling the plurality of users to modify one or more linkages between health regimen entities;
accepting input information from at least one user of the plurality of users of the at least one network health regimen information database, the input information including at least information indicating at least one of patterns or correlations between health regimen entities in the health regimen information linked by associative information;
automatically correlating one or more health regimen entities including adding associative information to the one or more data structures including at least one of pointers or identifiers indicating at least one or more linkages between two or more health regimen data entities based at least partly on the information indicating at least one of patterns or correlations between health regimen entities in the health regimen information linked by associative information and user modification of the one or more linkages between health regimen entities; and storing the associative information to the one or more data structures including at least one of pointers or identifiers indicating at least one or more linkages between the two or more health regimen data entities, wherein accessibility to the health regimen entities in the at least one network health regimen information database is modified in response to the input information received from the at least one user.

25. The system of claim 24, wherein the accepting input information from at least one user of the plurality of users of the at least one network health regimen information database includes:
accepting input information for integrating at least one report of an experience by at least one end-user into one or more health regimen data entities.

26. The system of claim 24, wherein the accepting input information from at least one user of the plurality of users of the at least one network health regimen information database includes:
adding information to one or more health regimen data entities.

27. The system of claim 24, wherein the accepting input information from at least one user of the plurality of users of the at least one network health regimen information database includes:
accepting input information for deleting information from one or more health regimen data entities.

28. The system of claim 24, wherein the accepting input information from at least one user of the plurality of users of the at least one network health regimen information database includes:
accepting input information for altering information associated with one or more health regimen data entities.

29. The system of claim 24, wherein the accepting input information from at least one user of the plurality of users of the at least one network health regimen information database includes:
accepting input information for accepting a change to one or more health regimen data entities from an end-user.

30. The system of claim 24, wherein the accepting input information from at least one user of the plurality of users of the at least one network health regimen information database includes:
accepting input information including a selection of at least one health regimen data entity.

31. The system of claim 24, wherein the automatically correlating one or more health regimen entities including adding associative information to the one or more data structures including at least one of pointers or identifiers indicating at least one or more linkages between two or more health regimen data entities comprises:
automatically correlating one or more health regimen entities including adding associative information to the one or more data structures including at least one of pointers or identifiers indicating at least one or more linkages between a first nesting health regimen data entity and a second nesting health regimen data entity that is linked with one or more other health regimen data entities.

32. The system of claim 24, wherein the automatically correlating one or more health regimen entities including adding associative information to the one or more data structures including at least one of pointers or identifiers indicating at least one or more linkages between two or more health regimen data entities comprises:
    automatically correlating one or more health regimen entities including adding associative information to the one or more data structures including at least one of pointers or identifiers indicating at least one or more linkages between a first nesting health regimen data entity and a second nested health regimen data entity that is linked with one or more other health regimen data entities.

33. The system of claim 24, wherein the automatically correlating one or more health regimen entities including adding associative information to the one or more data structures including at least one of pointers or identifiers indicating at least one or more linkages between two or more health regimen data entities comprises:
    automatically correlating one or more health regimen entities including adding associative information to the one or more data structures including at least one of pointers or identifiers indicating at least one or more linkages between a first nested health regimen data entity and a second nested health regimen data entity that is linked with one or more other health regimen data entities.

34. The system of claim 24, wherein the automatically correlating one or more health regimen entities including adding associative information to the one or more data structures including at least one of pointers or identifiers indicating at least one or more linkages between two or more health regimen data entities comprises:
    automatically correlating one or more health regimen entities including adding associative information to the one or more data structures including at least one of pointers or identifiers indicating at least one or more linkages between a first nested health regimen data entity and a second nesting health regimen data entity that is linked with one or more other health regimen data entities.

35. The system of claim 24, wherein the automatically correlating one or more health regimen entities including adding associative information to the one or more data structures including at least one of pointers or identifiers indicating at least one or more linkages between two or more health regimen data entities comprises:
    automatically correlating one or more health regimen entities including adding associative information to the one or more data structures including at least one of pointers or identifiers indicating at least one or more linkages between a first nested health regimen data entity and a second nesting health regimen data entity that is linked with one or more other health regimen data entities.

36. The system of claim 24, wherein the automatically correlating one or more health regimen entities including adding associative information to the one or more data structures including at least one of pointers or identifiers indicating at least one or more linkages between two or more health regimen data entities comprises:
    at least one of:
        automatically correlating one or more health regimen entities including adding associative information to the one or more data structures including at least one of pointers or identifiers indicating at least one or more linkages between a first nesting health regimen data entity and a second non-nested health regimen data entity that is linked with one or more other health regimen data entities;
        automatically correlating one or more health regimen entities including adding associative information to the one or more data structures including at least one of pointers or identifiers indicating at least one or more linkages between a first nested health regimen data entity and a second non-nesting health regimen data entity that is linked with one or more other health regimen data entities; or
        automatically correlating one or more health regimen entities including adding associative information to the one or more data structures including at least one of pointers or identifiers indicating at least one or more linkages between a first nested health regimen data entity and a second non-nested health regimen data entity that is linked with one or more other health regimen data entities.

37. The system of claim 24, wherein the plurality of users of the at least one network health regimen information database includes:
    at least one of an end-user, a vendor, or a publisher.

38. The method of claim 21 wherein the storing the associative information to the one or more data structures including at least one of pointers or identifiers indicating at least one or more linkages between the two or more health regimen data entities, wherein accessibility to the health regimen entities in the at least one network health regimen information database is modified in response to the input information received from the at least one user comprises:
    storing the associative information to the one or more data structures including at least one of pointers or identifiers indicating at least one or more linkages between the vitamin regimen data entity and the constituent substance data entity such that personal note information of the one or more personal notes data entities is provided in association with the vitamin regimen data entity.

* * * * *

UNITED STATES PATENT AND TRADEMARK OFFICE
CERTIFICATE OF CORRECTION

PATENT NO.       : 10,042,980 B2
APPLICATION NO.  : 11/283548
DATED            : August 7, 2018
INVENTOR(S)      : Edward K. Y. Jung et al.

Page 1 of 1

It is certified that error appears in the above-identified patent and that said Letters Patent is hereby corrected as shown below:

In the Claims

Column 23, Lines 50-51, Claim 35:
Change "between a first nested health regimen data entity and a second nesting health regimen"
To -- between a first nesting health regimen data entity and a second non-nesting health regimen --

Signed and Sealed this
Eleventh Day of September, 2018

Andrei Iancu
*Director of the United States Patent and Trademark Office*